(12) United States Patent
Porter

(10) Patent No.: US 11,712,542 B2
(45) Date of Patent: Aug. 1, 2023

(54) DYNAMIC CURVE ACCESS TOOL FOR COMPLEX ARCH ANATOMIES AND RADIAL ACCESS

(71) Applicants: STRYKER CORPORATION, Kalamazoo, MI (US); STRYKER EUROPEAN OPERATIONS LIMITED, County Cork (IE)

(72) Inventor: Stephen Porter, Piedmont, CA (US)

(73) Assignees: Stryker Corporation, Kalamazoo, MI (US); Stryker European Operations Limited, Carrigtwohill (IE)

(*) Notice: Subject to any disclaimer, the term of this patent is extended or adjusted under 35 U.S.C. 154(b) by 333 days.

(21) Appl. No.: 17/148,073

(22) Filed: Jan. 13, 2021

(65) Prior Publication Data

US 2022/0218948 A1 Jul. 14, 2022

(51) Int. Cl.
*A61M 25/01* (2006.01)
(52) U.S. Cl.
CPC . *A61M 25/0133* (2013.01); *A61M 2202/0007* (2013.01); *A61M 2202/0468* (2013.01)
(58) Field of Classification Search
CPC ...... A61B 1/00147; A61M 2025/0004; A61M 25/0105
See application file for complete search history.

(56) References Cited

U.S. PATENT DOCUMENTS

| | | | |
|---|---|---|---|
| 10,835,258 B1 * | 11/2020 | Pillai | A61B 17/12109 |
| 2004/0054322 A1 | 3/2004 | Vargas | |
| 2008/0249465 A1 | 10/2008 | Ryder et al. | |
| 2011/0276024 A1 | 11/2011 | Randolph et al. | |
| 2017/0239447 A1 * | 8/2017 | Yang | A61M 25/0053 |
| 2017/0304095 A1 * | 10/2017 | Syed | A61B 17/221 |
| 2018/0116684 A1 * | 5/2018 | Garrison | A61M 25/0043 |
| 2019/0254690 A1 * | 8/2019 | Cabiri | A61M 25/09 |
| 2020/0009351 A1 * | 1/2020 | Walzman | A61M 25/0041 |
| 2020/0205845 A1 * | 7/2020 | Yang | A61M 25/0108 |
| 2022/0118219 A1 * | 4/2022 | Walzman | A61F 2/954 |

OTHER PUBLICATIONS

PCT International Search Report and Written Opinion for International Appln. No. PCT/US2021/065256, application Stryker Corporation, dated Apr. 29, 2022 (11 pages).

* cited by examiner

*Primary Examiner* — Scott J Medway
(74) *Attorney, Agent, or Firm* — Vista IP Law Group, LLP

(57) ABSTRACT

An intravascular device comprises an elongated outer catheter body having a proximal catheter end, a distal catheter end, and an inner catheter lumen extending between the proximal catheter end and the distal catheter end. The intravascular device further comprises an elongated inner articulating member slidably disposed within the inner catheter lumen. The inner articulating member has a proximal member end and an articulatable distal member end. The intravascular device further comprises a control assembly mechanically coupled to the proximal catheter end and the proximal member end. The control assembly is configured for distally translating the outer catheter body over the inner articulating member, and for articulating the distal member end.

20 Claims, 24 Drawing Sheets

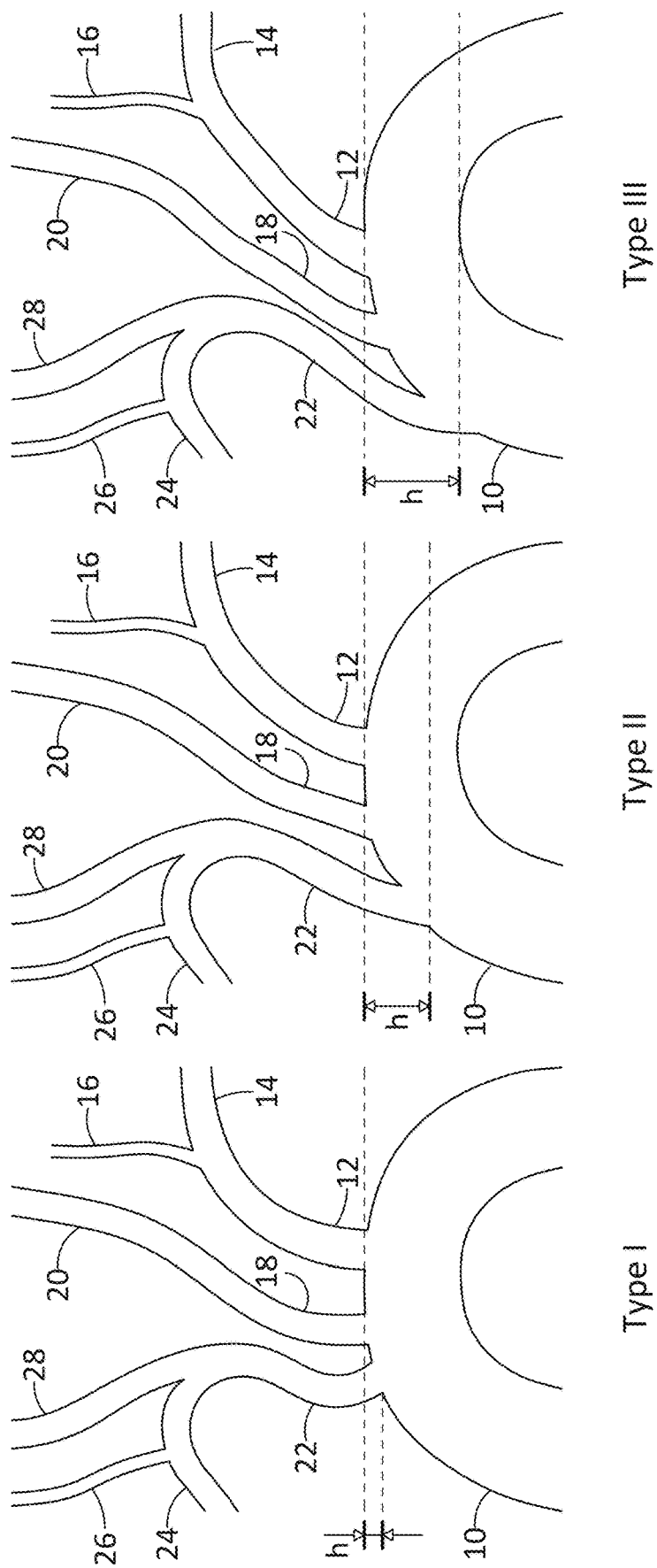

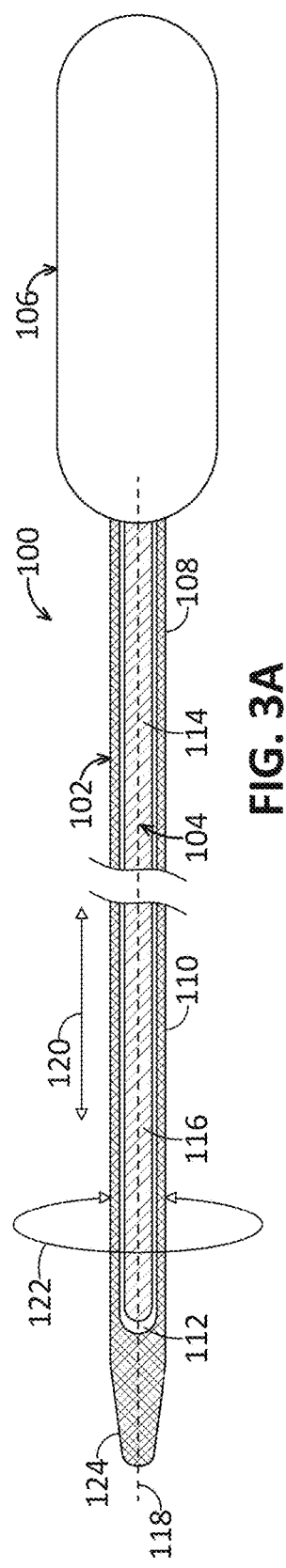
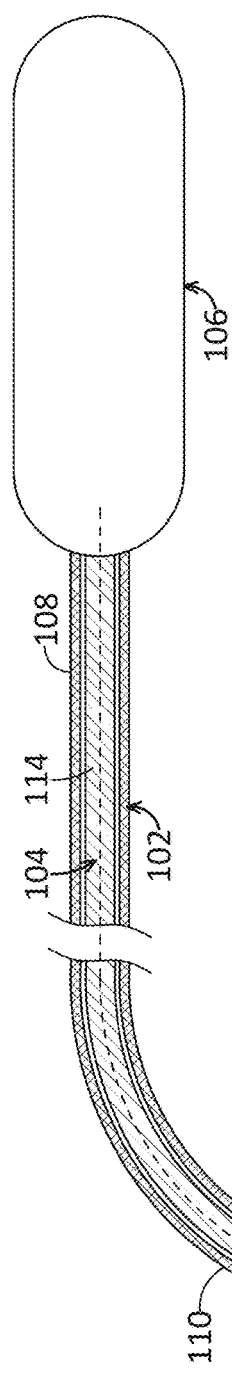
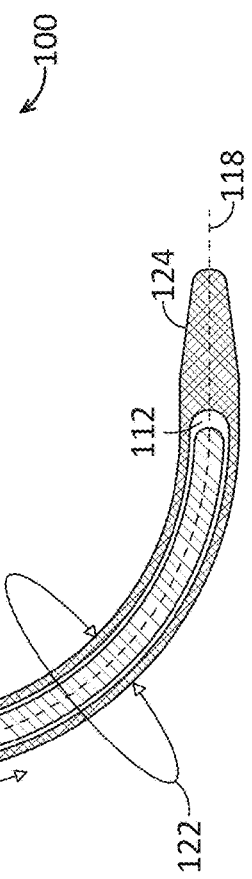
FIG. 3A
FIG. 3B

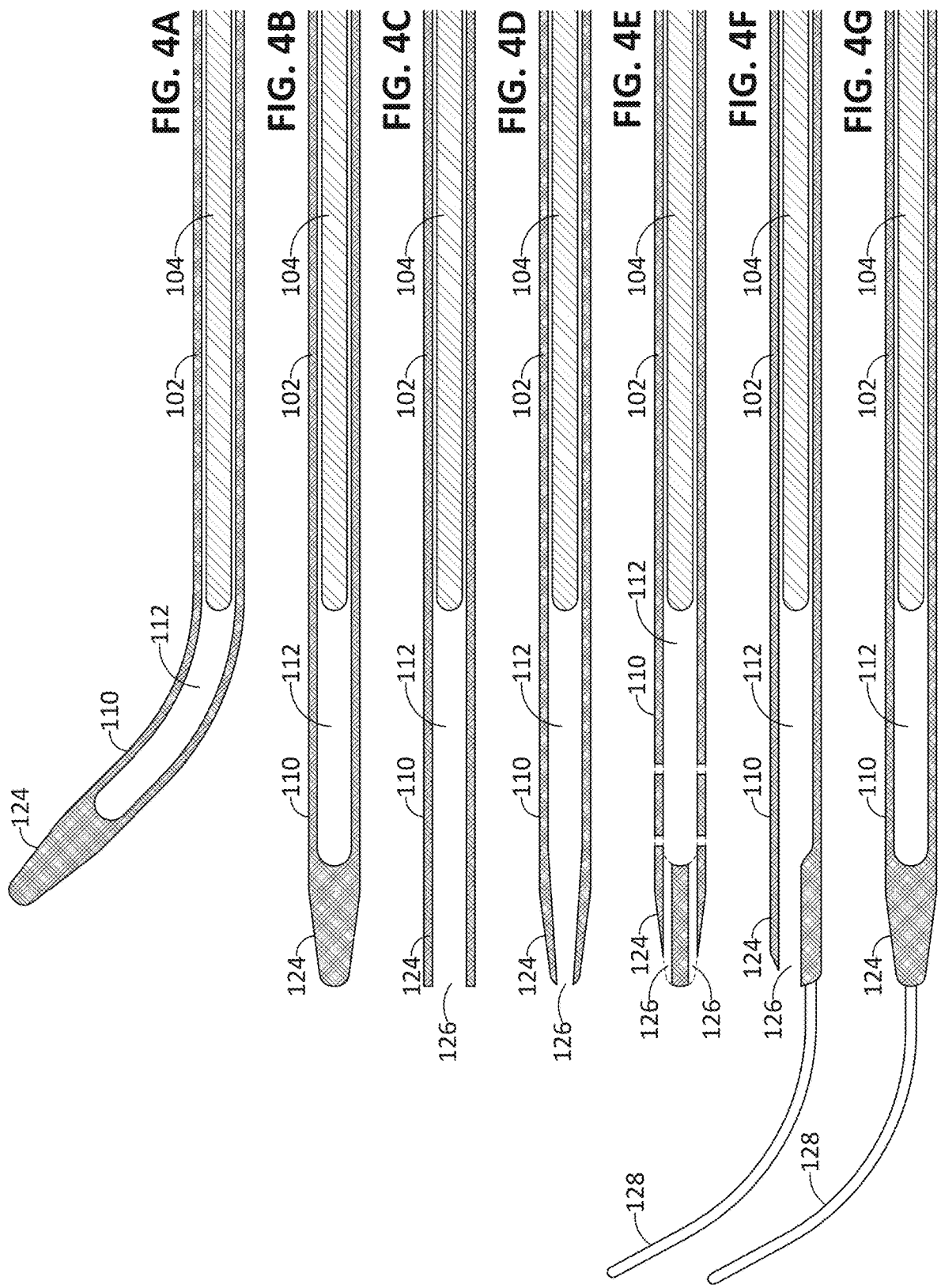

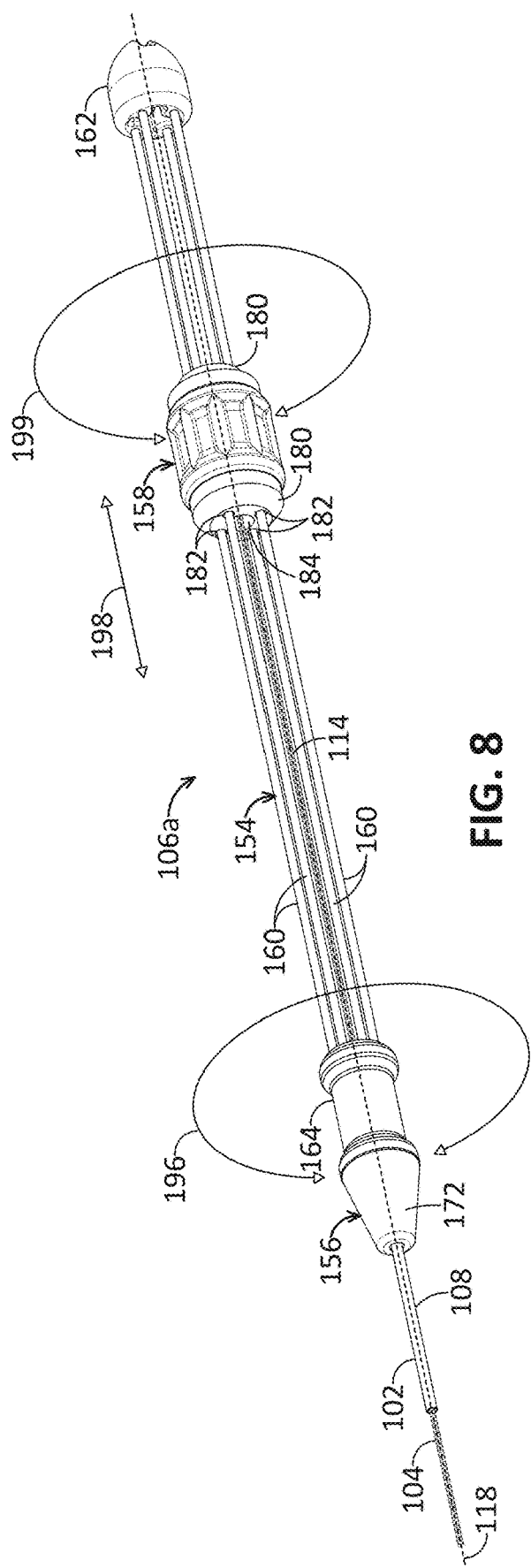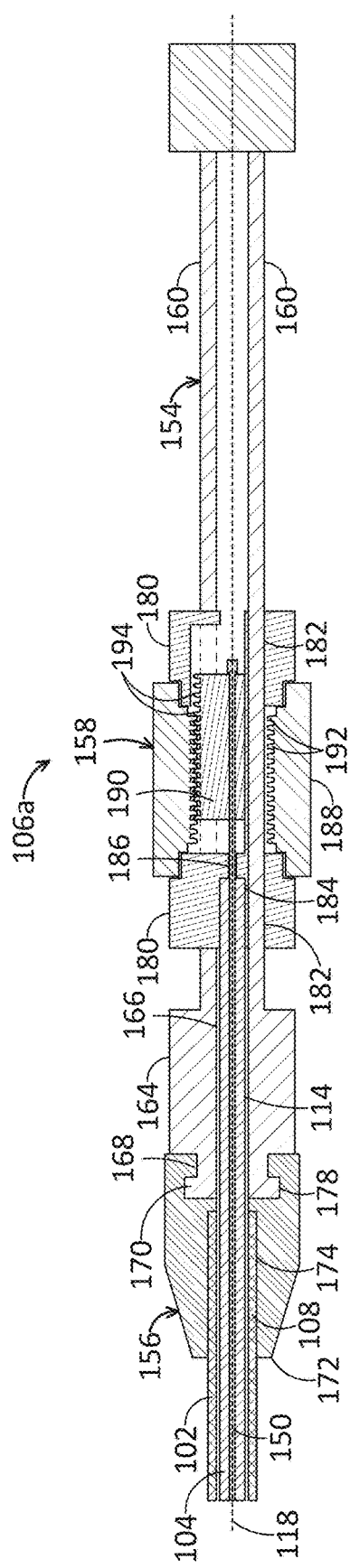

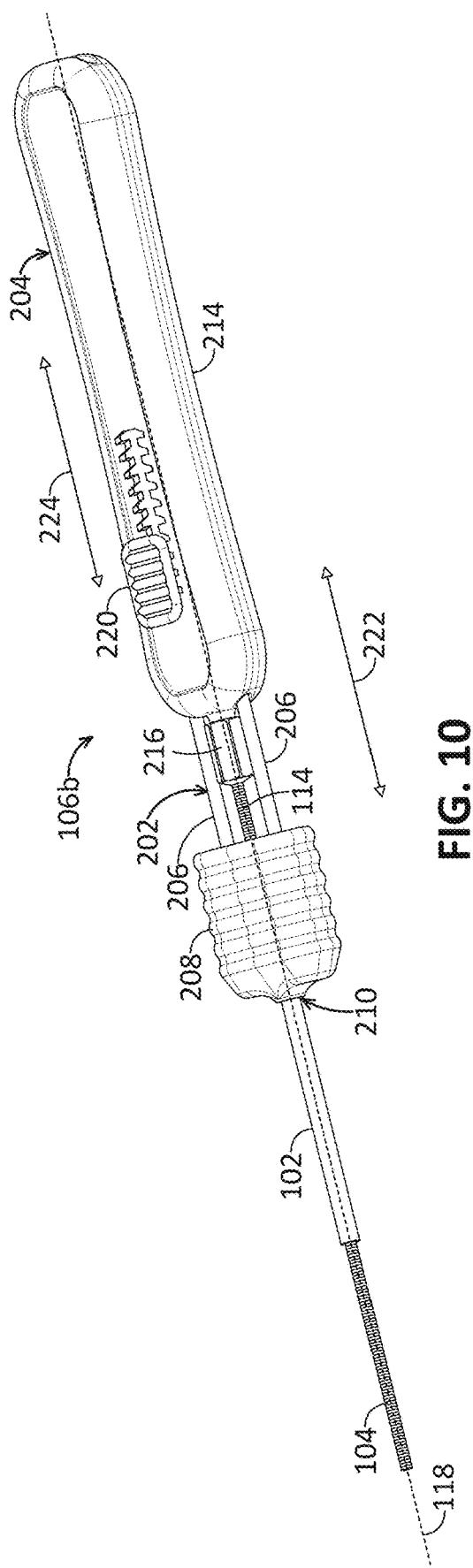
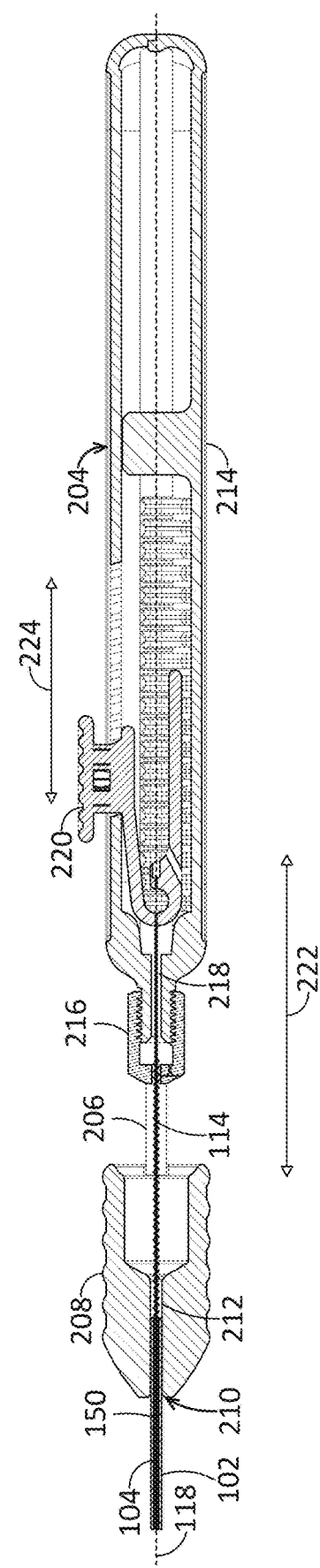
FIG. 10
FIG. 11

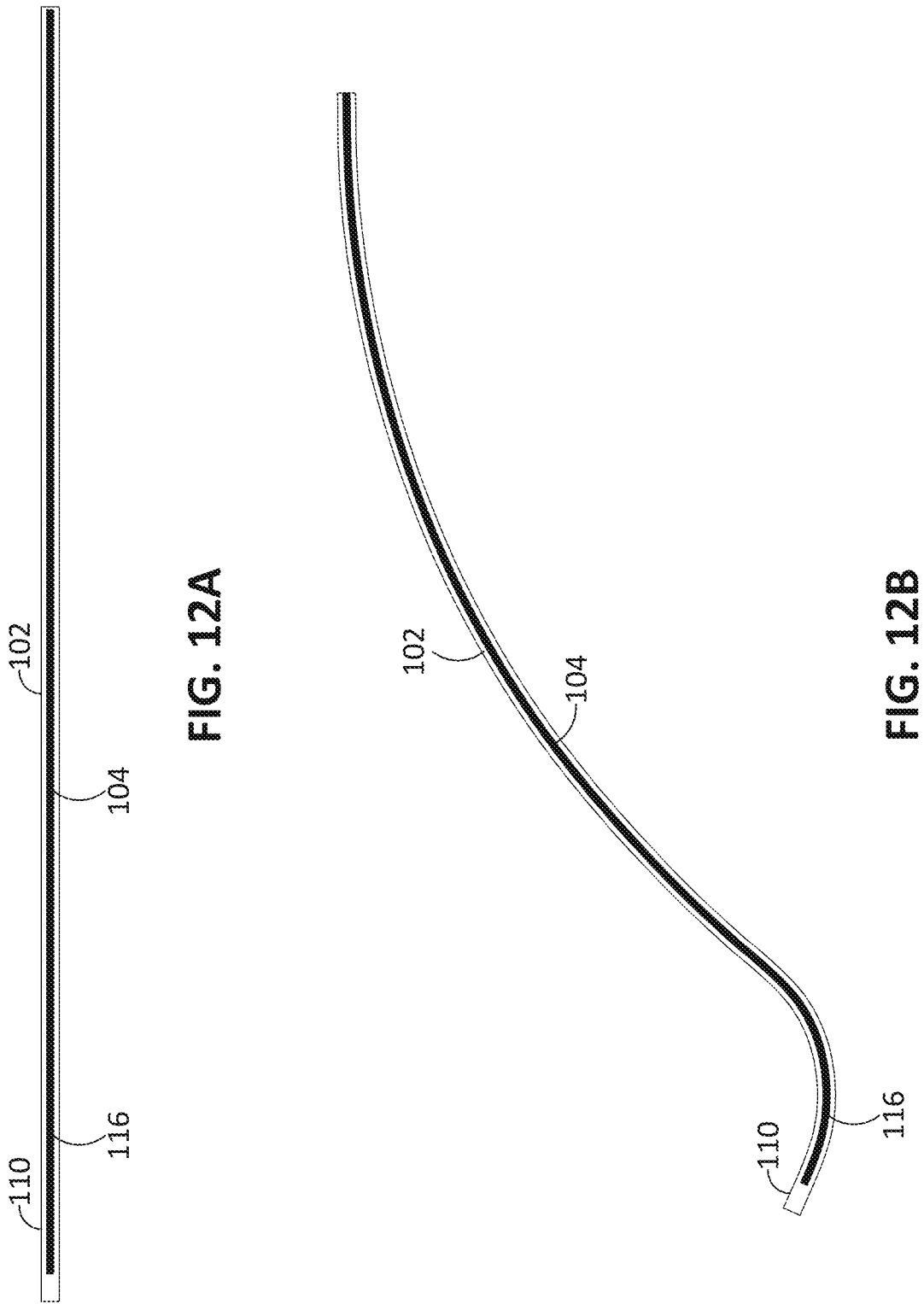

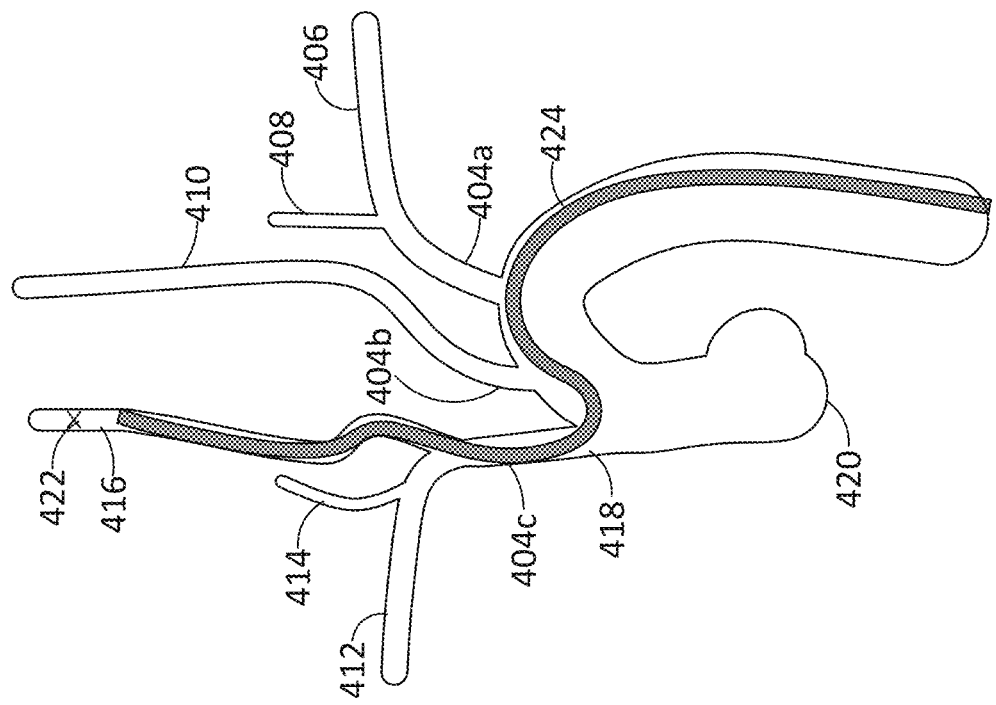
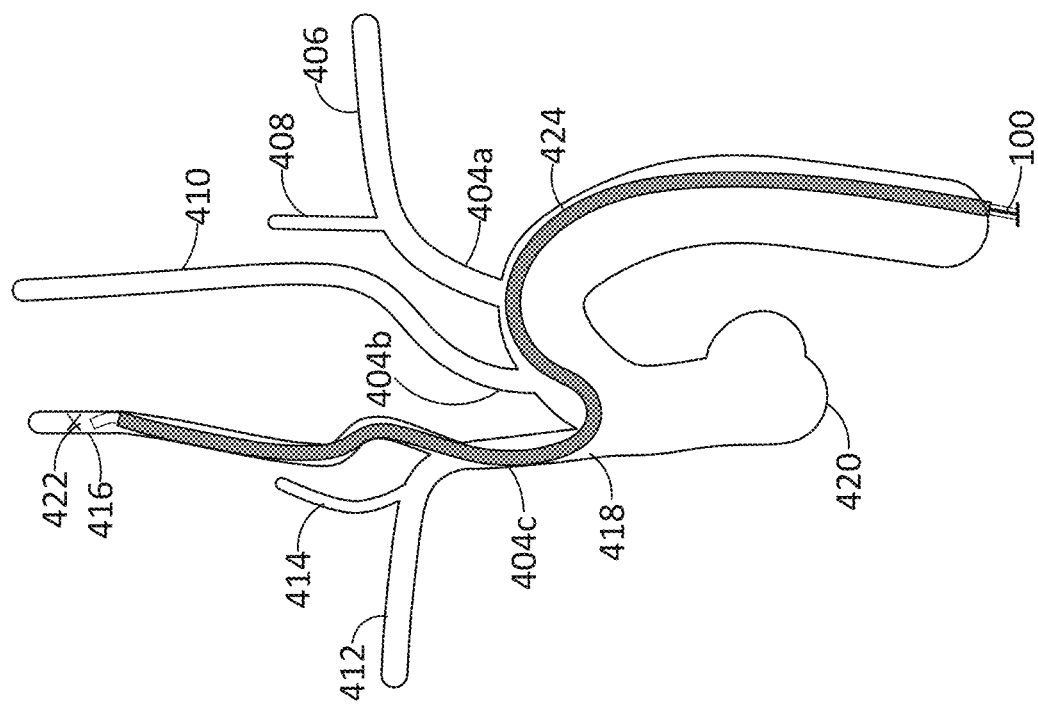
FIG. 14G
FIG. 14H

DYNAMIC CURVE ACCESS TOOL FOR COMPLEX ARCH ANATOMIES AND RADIAL ACCESS

FIELD OF THE INVENTION

The present disclosure relates generally to medical devices and intravascular medical procedures and, more particularly, to devices and methods for controlling deflection at the distal end of a catheter.

BACKGROUND

Therapeutic or diagnostic catheters are commonly used to perform medical procedures within very small spaces in a patient's body. Most of these medical procedures mandate precise catheter navigation. To access a target site within the human body from a remote location, a catheter is typically passed through one or more body lumens, such as through the vascular system, to the target site. When the vascular system is used, the catheter is inserted into an artery or vein percutaneously or through a relatively small incision in the patient's body. The catheter is then threaded through the patient's system of blood vessels to reach the desired target site. Often a pathway is created through the vasculature to the target site with the use of a delivery device, such as a guide catheter or long sheath, through which a therapeutic or diagnostic catheter can be guided to the target site.

The usefulness of guide catheters is largely limited by their ability to successfully navigate through small vessels and around tight bends in the vasculature, such as around the aortic arch. Access of the great vessels off the aortic arch pose challenges, especially when anatomical features require devices to follow a highly tortured or a not well supported path. To overcome some of these challenges, pre-shaped selective catheters have been developed to direct guide catheters or long sheaths by providing an internal guide rail over which the guide catheter or long sheath may traverse a selected path to reach the intended target location for the guide catheter or long sheath. Such pre-shaped selective catheters may have multiple axially spaced curves that allow access to the great vessels which originate from the aortic arch. Often times a diagnostic catheter is used for the same purpose as the selective catheter, selective catheters generally are different only in length so that they will fit inside a guide catheter or long sheath. For example, diagnostic and selective catheters having various types of pre-shaped distal ends (e.g., Simmons, Headhunter, Vitek, Bentson, Newton, Berenstein shapes) have been developed to both assist in negotiating twists and branches common in a patient's arterial or venous system and to maintain a shape once positioned within a target cavity, e.g., a chamber in the heart. However, since the pre-shaped curve is fixed into the selective catheter at the time of manufacture, the radius, extent of the curvature, and overall shape generally cannot be altered in-situ. Due to anatomical variations, extensive pre-surgical planning would be necessary to determine an appropriate curvature of the selective catheter. Current practice requires guesswork to select an existing shape that is the closest approximation to the patient's anatomical geometry.

In one particular therapeutic procedure, a stent may be deployed in one or more carotid arteries or their branches with the use of a guide catheter to treat atherosclerosis. The disease processes that take place in these vessels cause deterioration of the interior vessel walls, and diseased material that detaches from the interior vessels can be swept through the arterial system with successively decreasing vessel diameter until it becomes lodged in a vessel construction, causing the cessation of blood flow in the block area, leading to tissue death from loss of oxygenation. This disease process is the leading cause of strokes, heart attacks, and other debilitating or fatal events. As atherosclerosis in the carotid artery progresses, the risk of stroke increases, and it becomes necessary to intervene to prevent stroke or death from clots or vessel debris that becomes lodged in the brain, specifically related to disease of the internal carotid artery branch, which serves the brain, or the common carotid artery, which preceded it in the circulatory path. It should be noted that stroke is the third leading cause in the developing nations. 85% of all strokes are ischemic (due to brain circulation compromise) in nature and 20-30% of all ischemic strokes are caused by carotid artery atherosclerotic occlusive disease. For atherosclerotic occlusive disease of the internal or common carotid artery, one procedure performed by interventionalists (interventional radiologists, vascular surgeons, or interventional cardiologists) is the installation of a stent, which is an expanding cylindrical wire or plastic mesh that supports and stabilizes the disease area of the artery, and reduces the stenosis (narrowing) of the artery through a treatment known as angioplasty, whereby an inflatable balloon is used to momentarily expand the sent across the inner diameter of the vessel in the stenotic region.

Stenting of a carotid artery is a challenging procedure because accessing the left or right carotid artery can be dependent on the anatomical disposition of the aortic arch. For example, referring to FIG. 1A-1C, a typical human has an aortic arch 10 with three major arterial branches that leave aortic arch 10, including a first arterial branch 12 that forms the left subclavian artery (LSA) 14 and left vertebral artery (LVA) 16, a second arterial branch 18 that forms the left common carotid artery 20 (LCCA), and a third arterial branch (brachiocephalic trunk) 22 that forms the right subclavian artery (RSA) 24, right vertebral artery (RVA) 26, and right common carotid artery (RCCA) 28.

There are three types of arches defined by the height h of the top of the aortic arch 10 from the base location where the brachiocephalic trunk 22 attaches to the aortic arch 10. In a Type I arch, the height h is insignificant (h less than diameter of LCCA 20 or RCCA 28), as illustrated in FIG. 1A. In a Type II arch, the height h significantly increases (h between one and two times the diameter of LCCA 20 or RCCA 28), as illustrated in FIG. 1B, while in a Type III arch, the height h increases even more (h greater than two times diameter of LCCA 20 or RCCA 28), as illustrated in FIG. 1C. As the height of the aortic arch 10 increases, the procedures within the carotid arteries become more and more difficult due to the tortuous nature of the arterial connections to the aortic arch 10. For example, in Type III hostile aortic arches, as illustrated in FIG. 1C, the angle of origin of the second arterial branch 18 or third arterial branch 22 can be very acute, thus making access to the LCCA 20 or RCCA 28 difficult. Bovine arches are another example of difficult anatomies, in which the origin of the LCCA (18) emanates from the brachiocephalic trunk (22).

For example, an interventionalist may select between a femoral approach or a radial approach when accessing one of the arterial branches from the aortic arch 10. As illustrated in FIG. 2A, during a femoral approach, a catheter 30 may be introduced within the femoral artery, up the abdominal aorta to the descending aorta, and around the aortic arch 10 to one of the three arterial branches of the aortic arch 10. In contrast, as illustrated in FIG. 2B, during a radial approach, a catheter 30 may be introduced into and through the radial artery, through the brachial and axillary arteries, then along the RSA 24, and finally into the aortic arch 10. In one method, the catheter 30 will be inserted into a selected one of the arterial branches from the aortic arch 10 to provide a stable platform through which the interventional device (e.g., a stent delivery device) is to be introduced into the diseased artery. In other methods, the catheter 30 may serve as a diagnostic catheter for injecting imaging dye within one of the major arterial branches extending from the aorta. Oftentimes, a selective catheter with a pre-bent or pre-shaped distal end may be used to facilitate proper orientation of the guide catheter within the aortic arch 10 and subsequent introduction of the guide catheter into the relevant arterial branch of the aortic arch 10.

Interventional procedures in the neck or above the neck are challenging, particularly when confronted with hostile aortic arches, such as Type III or bovine arches or instances where the LCCA emanates from the arch at an acute angle. The interventional devices that are introduced through the guide catheter are often relatively stiff, and due to the tortuosity of the vessels originating from the aortic arch 10, the catheter 30, along with the interventional device, can become unstable and be pushed out into the aortic arch 10. Thus, it is important that the catheter 30 be distally introduced as far into the arterial branches of the aortic arch as possible in order to provide a stable platform for interventional devices to travel to their intended treatment location.

However, stroke intervention devices are becoming larger and larger, and as a result, the guide sheaths that provide the support platform for these larger intervention devices must become larger and more supportive. While newer more supportive and flexible guide catheter designs have been, and are continuing, to be developed, the challenge of traversing unsupported anatomical bends remains. Even if a selective catheter is used to facilitate proper orientation of the guide catheter within the aortic arch 10, the statically located curve at the distal end of the selective catheter prevents the selective catheter from being distally advanced deep into the selected arterial branch of the aortic arch 10 to achieve greater stability to additionally facilitate the advancement of a large supportive interventional device over the selective catheter.

There, thus, is an ongoing need to an improved means for manipulating a guide catheter within an anatomical vessel, such as one of the arterial branches from the aortic arch.

SUMMARY

In accordance with a first aspect of the present inventions, an intravascular device comprises an elongated outer catheter body having a proximal catheter end, a distal catheter end, and an inner lumen extending between the proximal catheter end and the distal catheter end. In one embodiment, the distal catheter end has one or more infusion openings. In another embodiment, the distal catheter end includes a distal wire tip. In still another embodiment, the distal catheter end is configured for being inserted into a branch of an aortic arch of a human.

The intravascular device further comprises an elongated inner articulating member slidably disposed within the inner lumen of the outer catheter body. The inner articulating member has a proximal member end and an articulatable distal member end.

The intravascular device further comprises a control assembly mechanically coupled to the proximal catheter end and the proximal member end. The control assembly configured for distally translating the outer catheter body over the inner articulating member, and for articulating the distal member end. In one embodiment, the control assembly is configured for articulating the distal member end into a single-curve planar shape. In another embodiment, the control assembly is configured for articulating the distal member end into a multi-curve shape. In still another embodiment, the control assembly is a manually operated control assembly. In yet another embodiment, the control assembly is releasably coupled to the proximal catheter end. In yet another embodiment, the intravascular device further comprises at least one pull wire operably connected between the distal member end and the control assembly, in which case, the control assembly is configured for articulating the distal member end by tensioning the pull wire(s).

In accordance with a second aspect of the present inventions, an intravascular device comprises an elongated inner articulating member configured for being slidably disposed within an inner lumen of the outer catheter body having a proximal catheter end, a distal catheter end, and an inner lumen extending between the proximal catheter end and the distal catheter end. In one embodiment, the distal catheter end is configured for being inserted into a branch of an aortic arch of a human. The inner articulating member has a proximal member end and an articulatable distal member end.

The intravascular device further comprises a control assembly mechanically coupled to the proximal member end. The control assembly is further configured for being releasably coupled to the proximal catheter end. The control assembly is further configured for distally translating the outer catheter body over the inner articulating member, and for articulating the distal member end. In one embodiment, the control assembly is configured for articulating the distal member end into a single-curve planar shape. In another embodiment, the control assembly is configured for articulating the distal member end into a multi-curve shape. In still another embodiment, the control assembly is a manually operated control assembly. In yet another embodiment, the control assembly is releasably coupled to the proximal catheter end. In yet another embodiment, the intravascular device further comprises at least one pull wire operably connected between the distal member end and the control assembly, in which case, the control assembly is configured for articulating the distal member end by tensioning the at least one pull wire.

In accordance with a third aspect of the present inventions, a method of performing a medical procedure on a patient using an intravascular device including an elongated outer catheter body having a distal catheter end and an inner catheter lumen, and an elongated inner member slidably disposed within the inner catheter lumen. The inner member has a distal member end.

The method comprises introducing the intravascular device within a vasculature of the patient (e.g., a femoral approach or a radial approach). The method further comprises distally advancing the intravascular device within the vasculature of the patient until the distal catheter end is adjacent an ostium of a blood vessel within the vasculature. In one method, the blood vessel is an arterial branch extending from an aortic arch (e.g., a Type III aortic arch) of the patient (e.g., one of a first arterial branch that forms a left subclavian artery (LSA) and a left vertebral artery (LVA) of the patient, a second arterial branch that forms a left common carotid artery (LCCA) of the patient, and a third arterial branch that forms a right subclavian artery (RSA), right vertebral artery (RVA), and right common carotid artery (RCCA) of the patient). If the arterial branch is the third arterial branch, further advancing the distal catheter end into the blood vessel may comprise advancing the distal catheter end into the RCCA. In another method, the distal catheter end is inserted into the ostium of the blood vessel by distally sliding the distal catheter end relative to the distal member end.

The method further comprises actively articulating the distal member end, such that the distal catheter end is pointed at the ostium of the blood vessel. The method further comprises inserting the distal catheter end into the ostium of the blood vessel, and distally sliding the distal catheter end relative to the distal member end, such that the distal catheter end is further advanced into the blood vessel. One method may further comprise advancing a guide catheter over the intravascular device, while the distal catheter end remains in the blood vessel, until the guide catheter reaches a target therapeutic site, and removing the intravascular device from the guide catheter while the guide catheter is at the target therapeutic site. This method may further comprise introducing a therapeutic device through the guide catheter until the therapeutic device is at the target therapeutic site, and performing a therapeutic procedure at the target therapeutic site using the therapeutic device. Another method may further comprise removing the inner member from the inner lumen of the outer catheter body, advancing a guide catheter through the inner lumen of the outer catheter body, while the distal catheter end remains in the blood vessel, until the guide catheter reaches a target therapeutic site, and removing the intravascular device from the guide catheter while the guide catheter is at the target therapeutic site. This other method may further comprise introducing a therapeutic device through the inner lumen of the outer catheter body until the therapeutic device is at the target therapeutic site, and performing a therapeutic procedure at the target therapeutic site using the therapeutic device. An optional method further comprises delivering an imaging dye within the blood vessel via the catheter assembly.

Other and further aspects and features of embodiments will become apparent from the ensuing detailed description in view of the accompanying figures.

BRIEF DESCRIPTION OF THE DRAWINGS

The drawings illustrate the design and utility of preferred embodiments of the disclosed inventions, in which similar elements are referred to by common reference numerals. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. Further, an aspect or an advantage described in conjunction with a particular embodiment of the disclosed inventions is not necessarily limited to that embodiment and can be practiced in any other embodiments even if not so illustrated.

In order to better appreciate how the above-recited and other advantages and objects of the disclosed inventions are obtained, a more particular description of the disclosed inventions briefly described above will be rendered by reference to specific embodiments thereof, which are illustrated in the accompanying drawings.

Figure 2B:
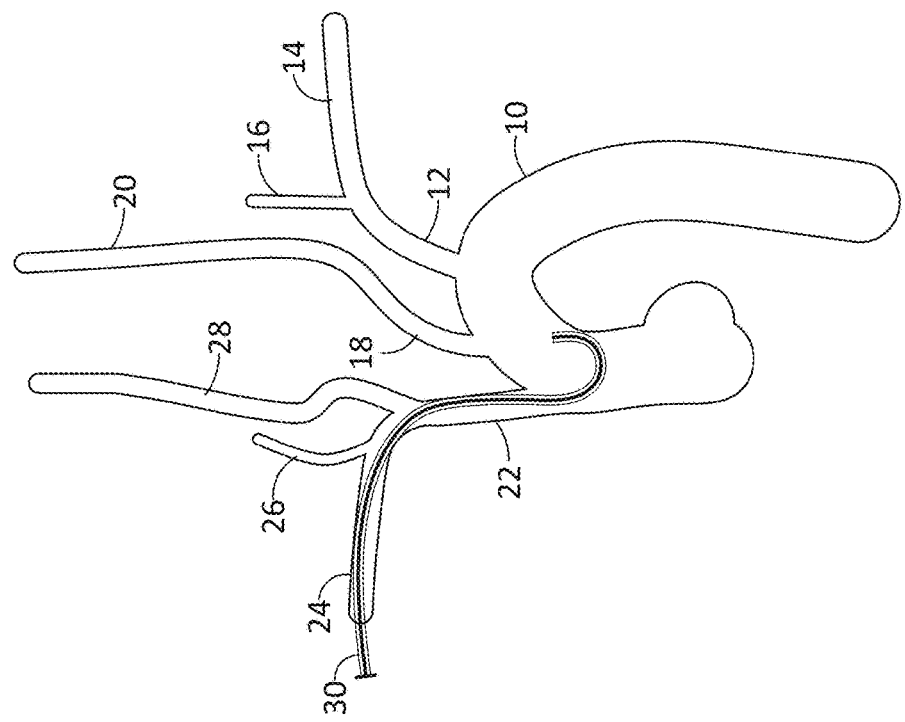
Figure 2A:
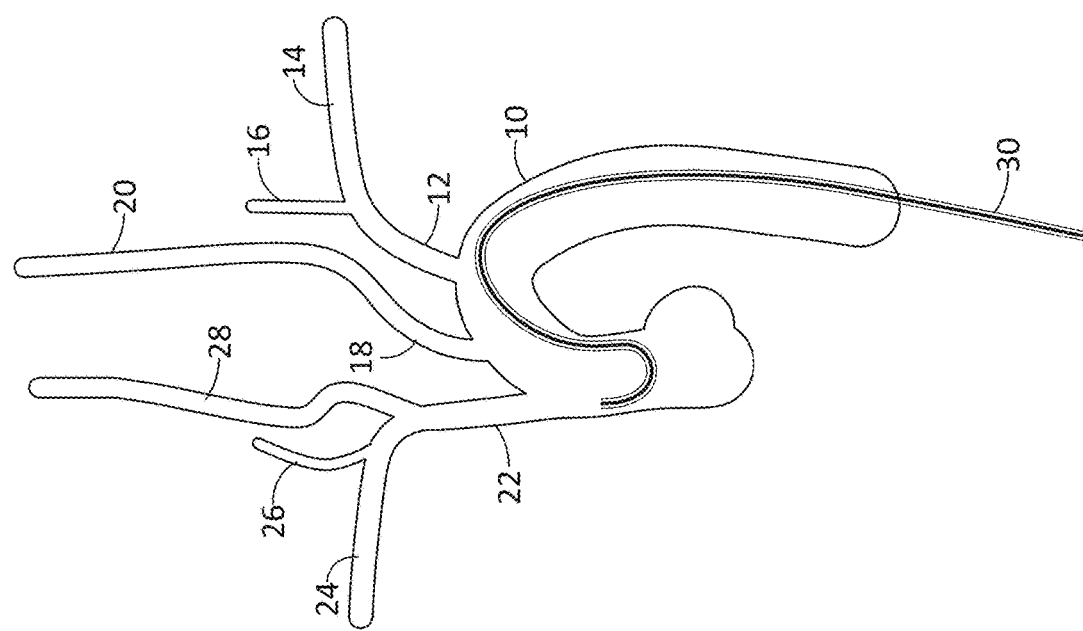
Figure 3C:
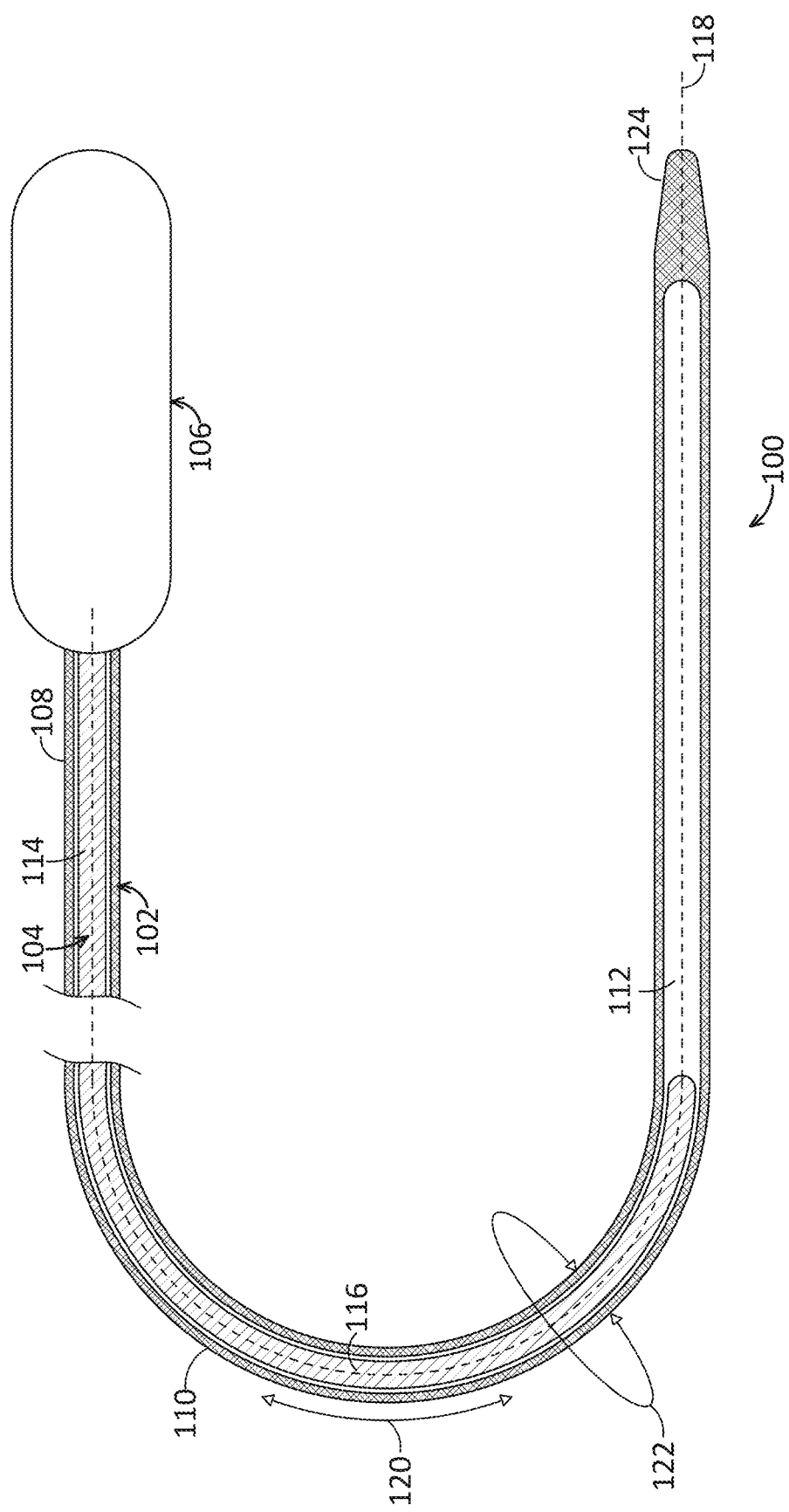
Figure 5:
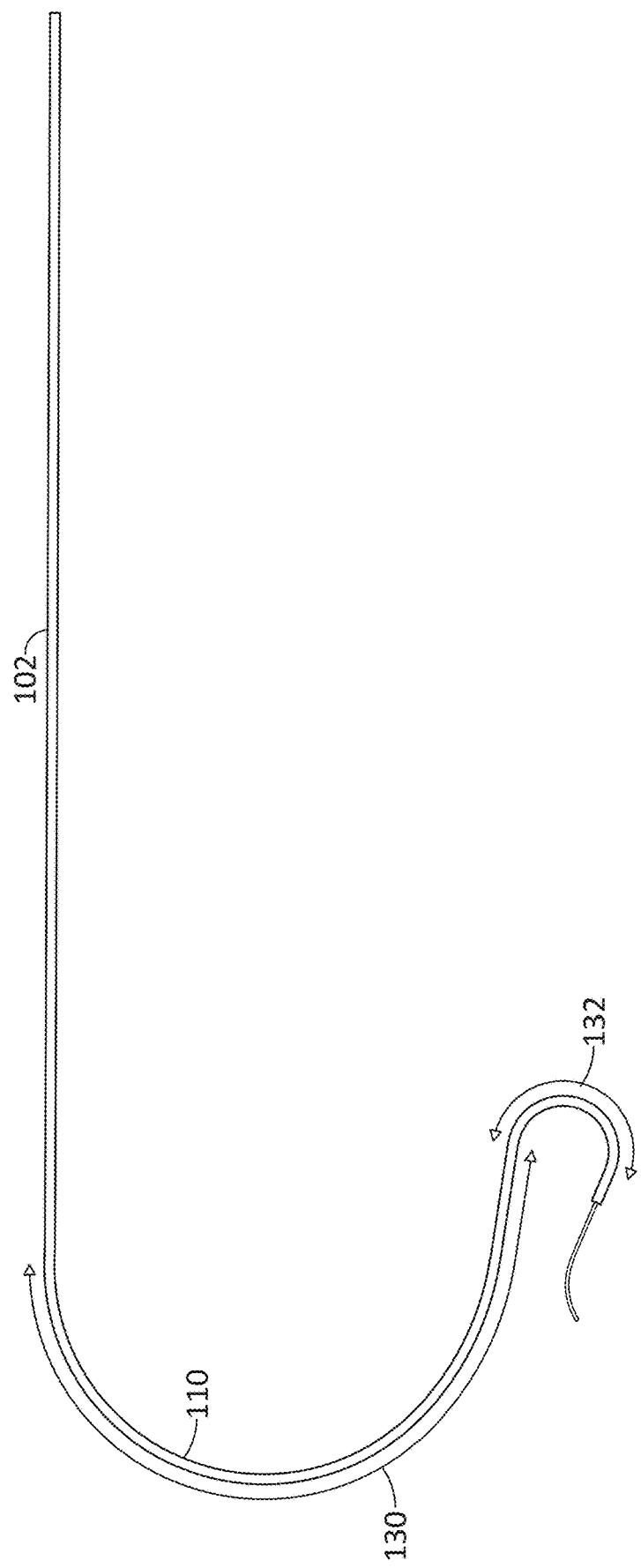
Figure 6:
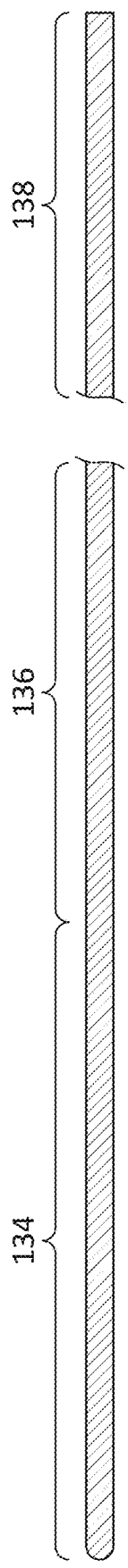
Figure 7:
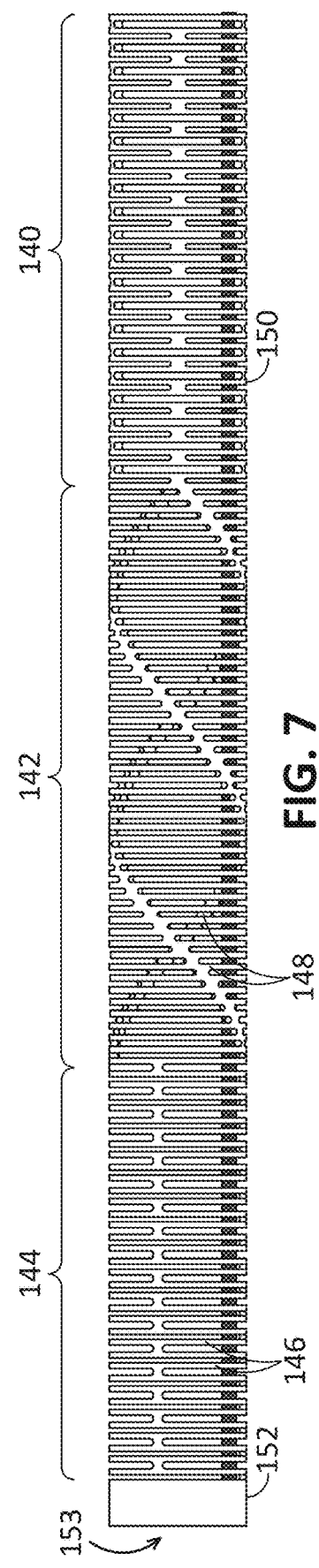
Figure 13:
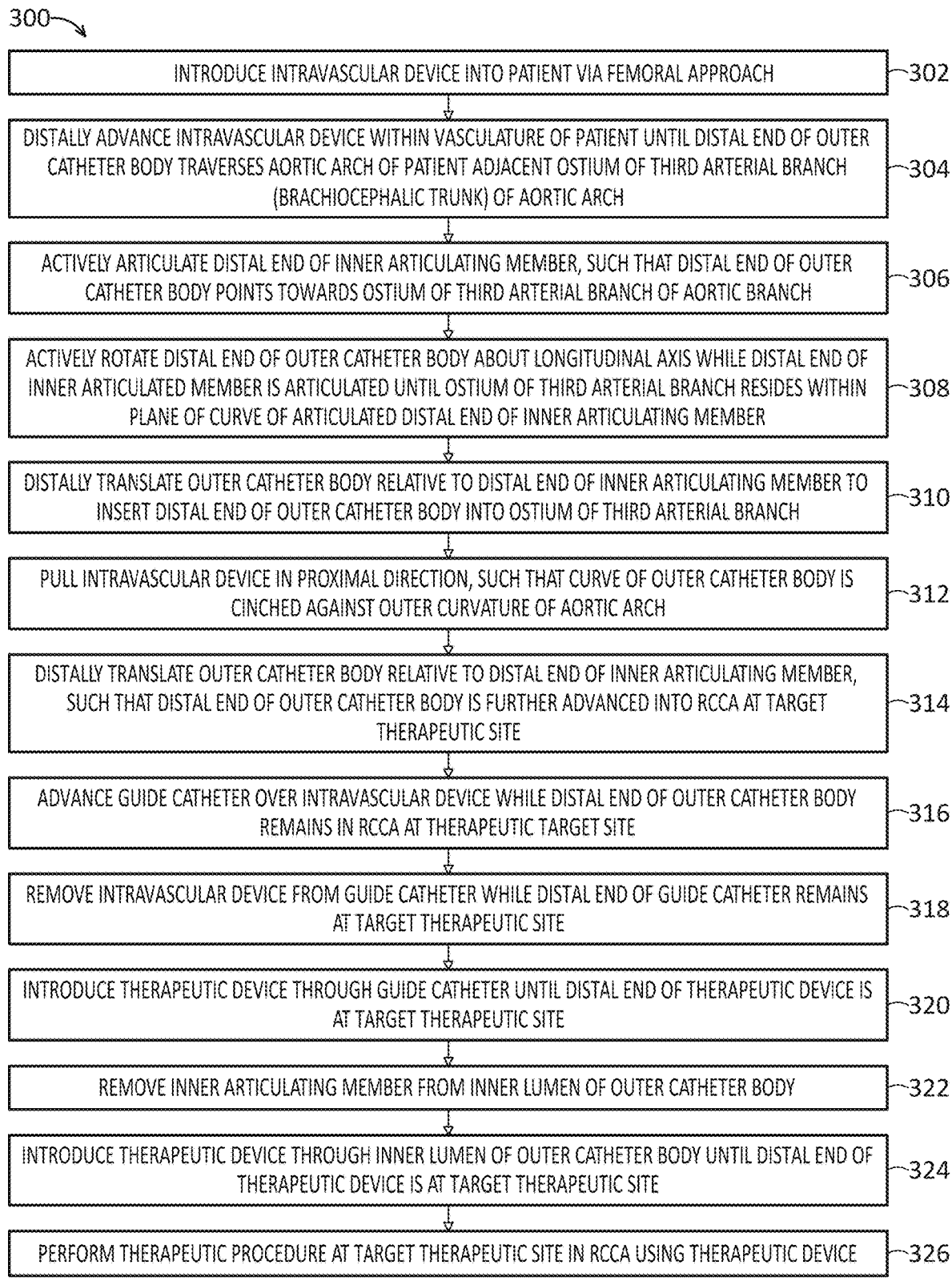
Figure 15:
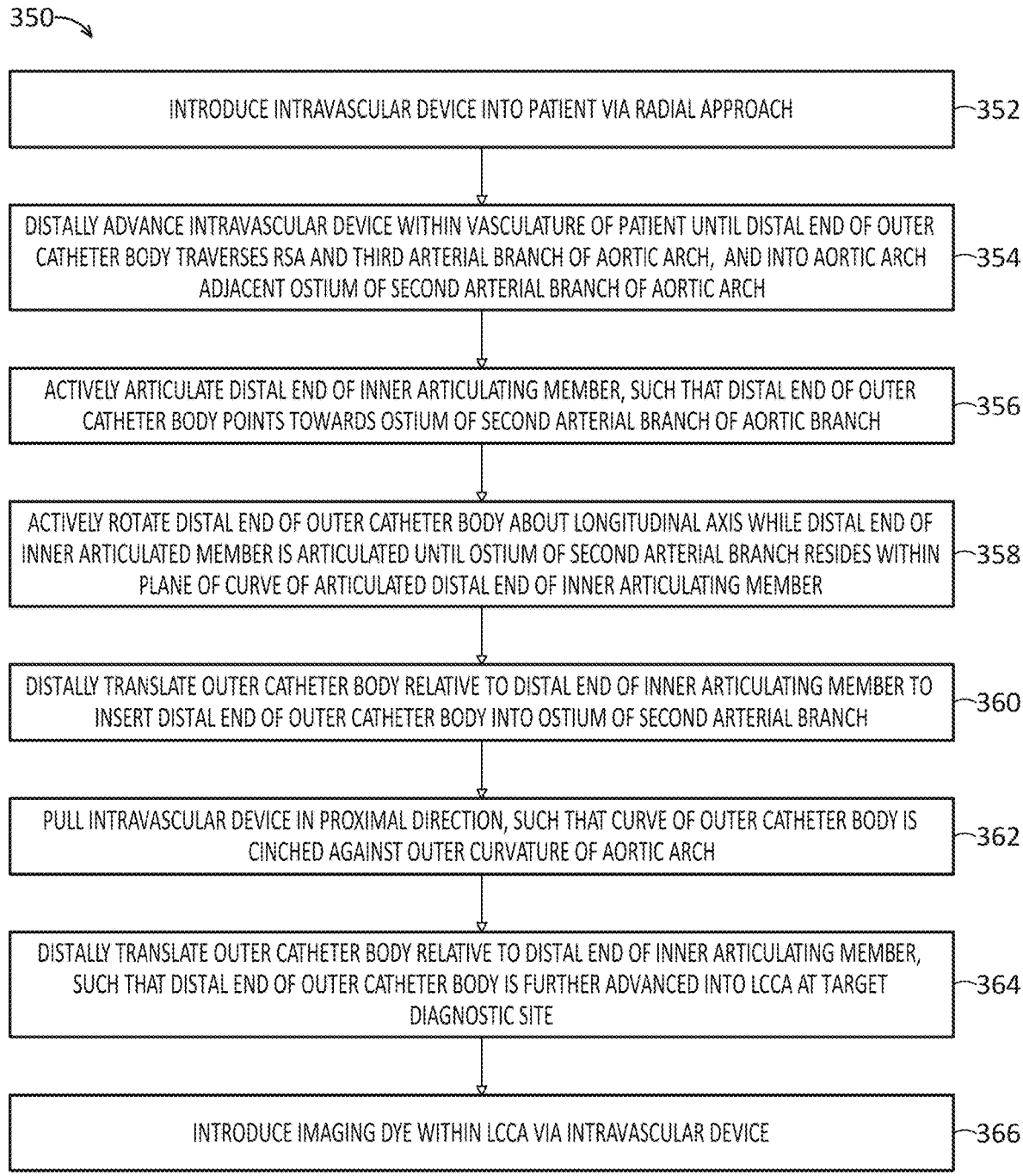

Understanding that these drawings depict only typical embodiments of the invention and are not therefore to be considered limiting of its scope, the invention will be described and explained with additional specificity and detail through the use of the accompanying drawings in which:

FIG. 1A is a plan view of an exemplary Type I aortic arch of a patient;

FIG. 1B is a plan view of an exemplary Type II aortic arch of a patient;

FIG. 1C is a plan view of an exemplary Type III aortic arch of a patient;

FIG. 2A is a plan view of a catheter introduced into a Type III aortic arch of a patient via the femoral approach;

FIG. 2B is a plan view of a catheter introduced into a Type III aortic arch of a patient via the right radial artery approach, including a plan view of the catheter of FIG. 2A, particularly showing the distal end of the catheter in a curved configuration;

FIG. 3A is a plan view of an intravascular device constructed in accordance with one exemplary embodiment of the present inventions, particularly shown in a straight configuration;

FIG. 3B is a plan view of the intravascular device of FIG. 3A, particularly shown in a curved configuration;

FIG. 3C is a plan view of the intravascular device of FIG. 3A, particularly shown in a curved, extended, configuration;

FIGS. 4A-4G are plan views of different distal ends of the intravascular device of FIG. 3A;

FIG. 5 is a plan view of one exemplary distal end of the intravascular device that assumes a complex curve;

FIG. 6 is a plan view of an exemplary inner articulating member of the intravascular device of FIG. 3A;

FIG. 7 is a plan view of one specific construction of the distal end of the inner articulating member of FIG. 6;

FIG. 8 is a perspective view of one exemplary embodiment of a control assembly that can be used by the intravascular device of FIG. 3A;

FIG. 9 is a longitudinal section of the control assembly of FIG. 8;

FIG. 10 is a perspective view of another exemplary embodiment of a control assembly that can be used by the intravascular device of FIG. 3A;

FIG. 11 is a longitudinal section of the control assembly of FIG. 10;

FIGS. 12A-12F are plan views of the distal end of the intravascular device of FIG. 3A, particularly shown in a sequence of different configurations;

FIG. 13 is a flow diagram illustrating one exemplary method of using the intravascular device of FIG. 3 to perform a therapeutic procedure in a patient;

FIGS. 14A-14I are plan views illustrating different steps used by the method of FIG. 13 to perform the therapeutic procedure in the patient;

FIG. 15 is a flow diagram illustrating one exemplary method of using the intravascular device of FIG. 3 to perform a diagnostic procedure in a patient; and FIGS. 16A-16G are plan views illustrating different steps used by the method of FIG. 15 to perform the therapeutic procedure in the patient.

DETAILED DESCRIPTION OF THE ILLUSTRATED EMBODIMENTS

Referring to FIGS. 3A-3C, one embodiment of an intravascular device 100 constructed in accordance with one embodiment of the present inventions will now be described. In the illustrated embodiment, the intravascular device 100 is described as a rail (especially used as an alternative to a traditional selective or diagnostic catheter) for subsequently advancing a guide catheter to a target therapeutic site within the body of a patient, which guide catheter can then be used to guide a therapeutic device (e.g., a catheter or other instrument) to the target therapeutic site. The intravascular device 100 lends itself well in facilitating the delivery of relatively stiff devices through unsupported curves, especially through Type III aortic arches via a femoral approach or any aortic arch configuration via a radial approach. However, it should be appreciated that the intravascular device 100 can take the form of any device, including a selective catheter, guidewire, or even a working catheter, itself, that is purposed to perform a medical procedure (therapeutic or diagnostic) that can benefit from accessing an ostium of a blood vessel, e.g., the ostium of an arterial branch off of the aortic arch of a patient.

In contrast to a selective catheter, which has a static curve that is in a static location on a catheter or even a conventional steerable catheter that would prevent the catheter from being distally advanced through an ostium and into the blood vessel, the intravascular device 100 can be shaped to direct the distal end of the intravascular device 100 towards or within the ostium of the blood vessel, and the distal end of the intravascular device 100 may be distally advanced relative to the shaped curve, thereby facilitating advancement of the distal end of the intravascular device 100 within the blood vessel, while the shaped curve remains in the location of the torturous anatomy for which the curve is facilitating transit therethrough.

To this end, the elongated intravascular device 100 generally comprises an outer catheter body 102, an inner articulating member 104 slidably disposed within the outer catheter body 102, and a control assembly 106. The outer catheter body 102 generally has a proximal end 108, a distal end 110, and an inner lumen 112 in which the inner articulating member 104 is slidably disposed. The inner articulating member 104 generally has a proximal end 114 and a distal end 116. The control assembly 106 is mechanically coupled to the proximal end 108 of the outer catheter body 102 and the proximal end 114 of the inner articulating member 104, and is configured for both articulating the inner articulating member 104 to form a curve in the inner articulating member 104 via energy transmission elements (and in particular one or more pull wires), and thus the elongated intravascular device 100 (see FIG. 3B), and to translate the outer catheter body 102 relative to the inner articulating member 104 in an axial direction 120 along a longitudinal axis 118 (see FIG. 3C). In the embodiment illustrated in FIG. 3B, the curve formed by the inner articulating member 104 is shown as a simple curve (a single bend), although as will be described in further detail below, the curve formed by the inner articulating member 104 may be a complex curve having multiple bends. Optionally, the control assembly 106 may be configured for translating the outer catheter body 102 relative to the inner articulating member 104 in a rotational direction 122 about the longitudinal axis 118.

The outer catheter body 102 may be constructed in a manner similar to most endovascular catheter shafts, and can be composed of a variety of materials using a variety of construction processes. The outer catheter body 102 is substantially pliable or flexible, such that when it is advanced into a patient, the outer catheter body 102 will conform, adopt, or match the shape or curvatures of blood vessels of the patient. Alternatively, the outer catheter body 102 may be semi-rigid, i.e., by being made of a stiff material, or by being reinforced with a coating or coil, to limit the amount of flexing.

The outer catheter body 102 is preferably about 2 French to 9 French in diameter, and between 80 cm to 150 cm in length. The outer catheter body 102 preferably has a cross-sectional geometry that is circular. However, other cross-sectional shapes, such as elliptical, rectangular, triangular, and various customized shapes, may be used as well. The outer catheter body 102 is preferably preformed of an inert, resilient plastic material that retains its shape and does not soften significantly at body temperature; for example, Pebax®, polyethylene, polyurethane, polyamide or Hytrel® (polyester). Alternatively, the outer catheter body 102 may be made of a variety of materials, including, but not limited to, metals and polymers.

The outer catheter body 102 may be composed of multiple layers of materials and/or multiple tube structures that exhibit a low bending stiffness, while providing a high axial stiffness along the longitudinal axis of the outer catheter body 102. Preferably, the outer catheter body 102 has adequate torsional rigidity, so that it can be rotated independently from the inner articulating member 104. Typical designs include a nitinol spine encapsulated in braid and any flexible, pliable, or suitable polymer material, a laser cut hypotube, or bio-compatible polymer material or a braided plastic composite structure composed of low durometer plastics (e.g., nylon-12, Pebax®, polyurethanes, polyethylenes, etc.).

The inner lumen 112 is disposed through the entire length of the outer catheter body 102. At least a portion of the inner lumen 112 of the outer catheter body 102 extending through the outer catheter body 102 may be formed by an inner polymer tube (e.g., 0.001" thick polytetrafluoroethylene (PTFE)). The distal end 110 of the outer catheter body 102 terminates in an atraumatic distal tip 124. In one embodiment illustrated in FIG. 4A, the distal catheter end 100 has a pre-shaped curve. In other embodiments illustrated in FIGS. 4B-4G, the distal catheter end 100 has a straight configuration. In the embodiments illustrated in FIGS. 4A-4B and 4G, the atraumatic distal tip 124 is closed or sealed, while in the embodiments illustrated in FIGS. 4C-4F, the atraumatic distal tip 124 has at least one infusion opening 126 that fluidly communicate with the inner lumen 112 of the outer catheter body 102 to allow for optional contrast injection. In the embodiments illustrated in FIGS. 4F-4G, the intravascular device 100 includes a distal wire tip 128 to facilitate entry into the ostium of the blood vessel.

Referring to FIG. 5, the distal end 116 of the inner articulating member 104 (shown in FIGS. 3A-3C), and thus the distal end 110 of the outer catheter tube 102, is configured for being gradually articulated from a straight configuration to a curved configuration into a multi-curve planar shape. In this embodiment, the distal end 116 of the inner articulating member 104 may be articulated into a Simmons-type shape, and in particular, a proximal curve 130 that bends in a plane to emulate the curvature of a typical aortic arch, and a distal curve 132 that bends in the same plane, but opposite the proximal curve 130, such that the distal end 116 of the inner articulating member 104, and thus the distal end 110 of the outer catheter body 102, points towards the ostium of an arterial branch off of the aortic arch of the patient, as will be described in further detail below. It should be appreciated that the multiple curved configuration illustrated in FIG. 5 is only exemplary, and alternative embodiments of the distal end 116 of the inner articulating member 104 may comprise only a single curve, or may comprise different types of compound curves having different shapes or different numbers of bends, including bends that are out-of-plane with each other, or even multiple compound curves.

Referring to FIG. 6, the inner articulating member 104 is functionality divided into three sections: a distal articulating section 134, an intermediate transition section 136, and a proximal shaft section 138.

The distal articulating section 134 preferably allows for a moderate degree of axial compression and optimal lateral flexibility. The distal articulating section 134 has several portions of differing rigidities. In an exemplary embodiment illustrated in FIG. 7, the distal articulating section 134 comprises a relatively flexible distal articulating region 140, which forms the distal curve 132, a relatively flexible proximal articulating region 144, which forms the proximal curve 130, and a relatively inflexible non-articulating region 142 located between the proximal articulating region 144 and the distal articulating region 140.

In the embodiment illustrated in FIG. 7, the distal articulating section 134 is formed of a slotted (e.g., micromachined or laser-cut) hypotube that tailors the flexibility, bending arc length, minimum bend radius and bending plane of the distal articulating section 134. In particular, the slotted hypotube has slots 146 that are strategically sized and located in a manner such that the articulating section 134 forms the proximal curve 130 coincident with the proximal articulating region 144 and the distal curve 132 coincident with the distal articulating region 140. The distal articulating section 134 further includes a pair of spiral struts 148 arranged in the non-articulating region 142 to add lateral rigidity thereto, such that the proximal articulating region 144 and distal articulating region 140 of the distal articulating section 134 predictably articulate about the non-articulating region 142 to form the proximal curve 130 and distal curve 132. In an alternative embodiment, instead of a laser cut hypotube, the distal articulating section 134 may be formed by having different outer tubes composed of a suitable polymer material (e.g., Pebax®). In this alternative case, to increase its axial rigidity and elastic properties, the distal articulating section 134 may comprise a braided layer (e.g., sixteen 0.0005"×0.003" spring temper 304V stainless steel wires braided at 68 picks per inch (ppi) in a 2-over-2 pattern) embedded within the outer polymer tubes, may comprise a coil with a varied pitch, or may comprise a slotted (e.g., micromachined) hypotube to tailor the flexibility and bending plane of the distal articulating section 134.

As briefly discussed above, the energy transmission conduit(s) are mechanical energy transmission conduits, and in particular, take the form of one or more pull wires that extend within the inner articulating member 104. In the illustrated embodiment, a single pull wire 150 is used. In the illustrated embodiment, the distal articulating section 134 comprises a distal tip ring 152 to which the distal end of the pull wire 150 is affixed, and a central lumen 153 through which the pull wire 150 extends back to the control assembly 106. Tensioning of the pull wire 150 via manipulation of the control assembly 106 (as will be described in further detail below) transforms the distal articulating section 134 from the straight configuration to the curved configuration.

The pull wire 150 may be a metallic wire, cable or filament, or it may be a polymeric wire, cable or filament. The pull wire 150 may also be made of natural or organic materials or fibers. The pull wire 150 may be any type of suitable wire, cable or filament capable of supporting various kinds of loads without deformation, significant deformation, or breakage. Although mechanical energy transmission conduit(s) have been described as being a pull wire, it should be appreciated that the mechanical energy transmission conduits should not be limited to pull wires. For example, the mechanical transmission conduit(s) may take the form of small diameter tubes or rods that are axially rigid, but laterally flexible. Furthermore, in alternative embodiments of the intravascular device 100, non-mechanical, e.g., fluid transmission conduits (e.g., hydraulic or pneumatic), electrical transmission conduits (i.e., electrical wires), electromagnetic energy (e.g., optical) transmission conduits, etc., may be used as energy transmission conduits. Essentially, any energy transmission conduit capable of transmitting any energy from the proximal end 114 to the distal end 116 of the inner articulating member 104 for articulating the distal articulating section 134 to form the proximal curve 130 and distal curve 132.

In order to impart different forces along the distal end 116 of the inner articulating member 104 to create the proximal curve 130 and distal curve 132, the pull wire 150 is slidably disposed, and floats, within the central lumen 153 extending through the inner articulating member 104. In an alternative embodiment, two pull wires may extend through two pull wire lumens (not shown) extending through the inner articulating member 104. In this case, the pull wire lumens may be constructed of a low friction material or may simply be unsupported tubular cavities in which the pull wires respectively float, and may be provided in the inner articulating member 104 in a 180-degree circumferentially spaced apart relationship.

As will be described in further detail below, the proximal end of the pull wire 150 is operatively coupled to the control assembly 106, while the distal end of the pull wire 150 is affixed to the distal end 116 of the inner articulating member 104, such that operation of the pull wire 150 via manual actuation of the control assembly 106 applies or modifies a force or tension to the distal end 116 of the inner articulating member 104, which may articulate to create the proximal curve 130 and distal curve 132. In the illustrated embodiment, the portion of the outer catheter body 102 surrounding the distal articulating section 134 of the inner articulating member 104 is resilient, such that releasing the pull wire 150 via manual actuation of the control assembly 106 will release the internal force or tension on the distal articulating section 134 of the inner articulating member 104, allowing the distal articulating section 134 to return to a straight configuration.

The intermediate transition section 136 resists axial compression to clearly define the proximal end of the distal articulating section 134 and transfer the motion of the pull wire 150 to the distal articulating section 134, while maintaining lateral flexibility to allow the intravascular device 100 to track over tortuous anatomies. The intermediate transition section 136 may be formed of an outer tube composed of a slotted hypotube or a suitable polymer material (e.g., Pebax®).

The proximal shaft section 138 gradually transitions the inner articulating member 102 from the intermediate transition section 136 to the more rigid remaining portion of the inner articulating member 102 by having portions of differing rigidities formed by having different sections of slotted hypotube configurations or different outer tubes composed of a suitable polymer material (e.g., Pebax®). To increase its axial rigidity of any polymer tube segments, the proximal shaft section 138 may comprise a double braided layer (e.g., sixteen 0.0005"×0.003" spring temper 304V stainless steel wires braided at 68 picks per inch (ppi) in a 2 over 2 pattern) embedded within the outer polymer tubes.

As briefly discussed above, the control assembly 106 is configured for articulating the distal end 116 of the inner articulating member 104 between a straight configuration and a curved configuration, translating the outer catheter body 102 over the inner articulating member 104 along the longitudinal axis 118, and optionally for rotating the outer catheter body 102 relative to the inner articulating member 104 about the longitudinal axis 118. In the illustrated embodiment, the control assembly 106 is a manually operated control assembly (i.e., an interventionalist manipulates the control assembly 106 via their hand or hands). In an alternative embodiment, the control assembly 106 may be automated, e.g., via a robotic device.

In the case where the intravascular device 100 serves as a rail for the subsequent introduction of a guide catheter or other device, at least a portion of the control assembly 106 may be releasably coupled to the outer catheter body 102. Thus, the control assembly 106, along with the inner articulating member 104 coupled thereto, can be pulled out of the inner lumen 112 of the outer catheter body 102, leaving the outer catheter body 102 in the vasculature of the patient to be used as a rail for a subsequently introduced guide catheter. The inner articulating member 104, along with the attached control assembly 106, may be packaged and sold with the outer catheter body 102, to form the intravascular device 100, or the inner articulating member 104, along with the attached control assembly 106, may be packaged and sold as a stand-along device, and then subsequently coupled to the outer catheter body 102, to form the intravascular device 100. In an alternative embodiment, the outer catheter body 102 in the intravascular device 100 takes the form of a guide catheter. In this case, the inner articulating member 104, along with the attached control assembly 106, may be packaged and sold as an introducer, and then subsequently coupled to the guide catheter 102, to form the intravascular device 100. Thus, the control assembly 106, along with the inner articulating member 104 coupled thereto, can be pulled out of the inner lumen 112 of the guide catheter 102, leaving the guide catheter 102 in the vasculature of the patient for subsequent introduction of a therapeutic device therethrough.

Referring now to FIGS. 8 and 9, one exemplary embodiment of a control assembly 106a that can be used in the intravascular device 100 illustrated in FIGS. 3A-3B will be described. The control assembly 106 generally comprises a frame 154, a rotation actuator 156 carried by the frame 154, and a combined axial translation/articulation actuator 158 carried by the frame 154.

The frame 154 comprises at least one slide rod 160 (and in this case, four slide rods), a proximal end cap 162 affixing the proximal ends of the slide rods 160 relative to each other, and a distal end cap 164 affixing the distal ends of the slide rods 160 relative to each other. As best shown in FIG. 9, the distal end cap 164 has a lumen 166 through which the proximal end 114 of the inner articulating member 104 is slidably disposed, and a reduced boss 168 having an annular ridge 170.

The rotational actuator 156 comprises a nose 172 having a distal lumen 174 in which the proximal end 108 of the outer catheter body 102 is affixed, and a proximal annular cavity 176 in which the annular ridge 170 of the reduced boss 168 is rotationally disposed. Thus, the nose 172 may be rotated in a bi-directional direction 196 about a longitudinal axis 118 relative to the distal end cap 164, thereby rotating the outer catheter body 102 about the longitudinal axis 118 relative to the frame 154. In the case where at least a portion of the control assembly 106a is releasably coupled to the proximal end 108 of the outer catheter body 102, the nose 172 may be releasably coupled to the proximal end 108 of the outer catheter body 102, e.g., using a threaded arrangement (not shown).

The axial translation/articulation actuator 158 comprises a housing 180 having at least one lumen 182 (and in this case, four lumens) through which the slide rods 160 of the frame 154 are slidably disposed. The housing 180 further has a distal opening 184 in which the proximal end 114 of the inner articulating member 104 is affixed. Thus, the frame 154 may be axially translated along the longitudinal axis 118 in a bi-directional direction 198 relative to the housing 180 of the axial translation/articulation actuator 158, thereby axially translating the outer catheter body 102 along the longitudinal axis 118 relative to the inner articulating member 104.

As best shown in FIG. 9, the housing 180 also has a reduced diameter lumen 186 in communication with the distal opening 184, and through which the pull wire 150 is slidably disposed. The axial translation/articulation actuator 158 further comprises a rotational gear in the form of a pinion collar 188, which is rotatably slidable about the housing 180, and a linear gear in the form of a rack 190, which is axially slidable within the housing 180. The pinion collar 188 has internal threads 192, and the rack has a linear row of teeth 194 that engage the internal threads 192 of the pinion collar 188. The rack 190 has a lumen 196 in which the proximal end of the pull wire 150 is affixed.

Thus, the pinion collar 188 may be rotated about the longitudinal axis 118 relative to the housing 180 in a bi-directional direction 199, thereby either proximally translating the pull wire 150 within the inner articulating member 104 that increases the articulation of the distal end 116 of the inner articulating member 104, or distally translating the pull wire 150 within the inner articulating member 104 that decreases the articulation of the distal end 116 of the inner articulating member 104.

It should be appreciated that, although only one specific embodiment of a control assembly 106a has been described, any control assembly capable of distally translating the outer catheter body 102 over the inner articulating member 104 and articulating the distal end 116 of the inner articulating member 104 between a straight configuration and a curved configuration may be employed.

For example, referring to FIGS. 10 and 11, an alternative embodiment of a control assembly 106b will described. Like the control assembly 106a described above, the control assembly 106b is mechanically coupled to the proximal end 108 of the outer catheter body 102 and the proximal end 114 of the inner articulating member 104. The control assembly 106b comprises a frame 202 and a combined axial translation/articulation actuator 204 carried by the frame 202.

The frame 202 comprises at least one slide rod 206 (and in this case, two slide rods) and a distal end cap 208 affixing the distal ends of the slide rods 206 relative to each other. As best shown in FIG. 11, the distal end cap 208 has a distal opening 210 in which the proximal end 108 of the outer catheter body 102 is affixed, and a through lumen 212 through which the proximal end 114 of the inner articulating member 104 is slidably disposed. In the case where at least a portion of the control assembly 106b is releasably coupled to the proximal end 108 of the outer catheter body 102, the nose distal end cap 208 may be releasably coupled to the proximal end 108 of the outer catheter body 102, e.g., using a threaded arrangement (not shown).

The axial translation/articulation actuator 204 comprises a handle body 214 configured for being manually grasped by an operator, and ergonomically molded to allow an operator to more easily manipulate the outer catheter body 102 and inner articulating member 104. In the illustrated embodiment, the handle body 214 has a fileted rectangular cross-section, although in alternative embodiments, the handle body 214 may have any cross-section that allows the operator to firmly grasp it, e.g., a circular or hexagonal cross-section. The handle body 214 has at least one blind lumen (not shown) (and in this case, two blind lumens) in which the slide rods 206 of the frame 202 are slidably disposed. The proximal end 114 of the inner articulating member 104 is affixed to the handle body 214 via a connector 216. Thus, the distal end cap 208 and affixed frame 202 of may be axially translated along the longitudinal axis 118 in a bi-directional direction 222 relative to the axial translation/articulation actuator 204, thereby axially translating the outer catheter body 102 along the longitudinal axis 118 relative to the inner articulating member 104.

The handle body 214 has a lumen 218 in communication with the connector 216, and through which the pull wire 150 is slidably disposed. The axial translation/articulation actuator 204 further comprises a slide mechanism 220 slidably disposed axially within an external slot 223 of the handle body 214. The proximal end of the pull wire 150 is affixed to the slide mechanism 220. Thus, the slide mechanism 220 may be slid along the longitudinal axis 118 in a bi-directional direction 224 relative to the handle body 214 in the proximal direction, thereby proximally translating the pull wire 150 within the inner articulating member 104 that increases the articulation of the distal articulating section 134 of the inner articulating member 104, and may be slid along the longitudinal axis 118 relative to the handle body 214 in the distal direction, thereby distally translating the pull wire 150 within the inner articulating member 104 that decreases the articulation of the distal end 116 of the inner articulating member 104.

Referring now to FIGS. 12A-12F, one technique of manipulating the control assembly 106 to perform a sequence of articulation and axial translation maneuvers will be described. As illustrated in in FIG. 12A, the distal end 110 of the outer catheter tube 102 is in its proximal-most position relative to the inner articulating member 104, and the distal end 116 of the inner articulating member 104, and thus the distal end 110 of the outer catheter tube 102, is in a straight configuration. In this configuration, in the case where the intravascular device 100 comprises the control assembly 106a (see FIGS. 8-9), the housing 180 of the axial translation/actuation actuator 158 is in its distal-most position relative to the frame 154, and the pinion collar 188 is rotated about the longitudinal axis 118 in a neutral position relative to the housing 180 of the axial translation/articulation actuator 158. In the case where the intravascular device 100 comprises the control assembly 106b (see FIGS. 10-11), the handle body 214 of the axial translation/actuation actuator 204 is in its distal-most position relative to the frame 202, and the slide mechanism 220 is at its distal-most position relative to the handle body 214 of the axial translation/articulation actuator 204.

Figure 12C:
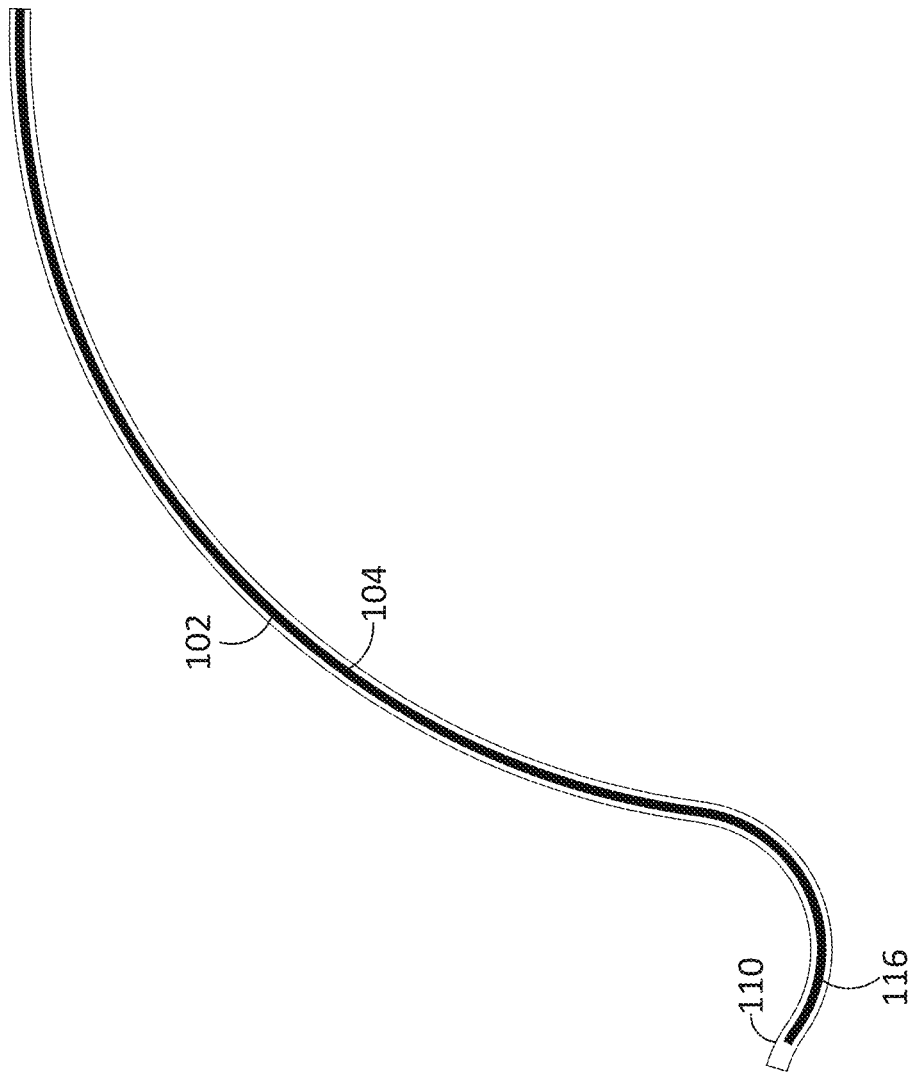
Figure 12E:
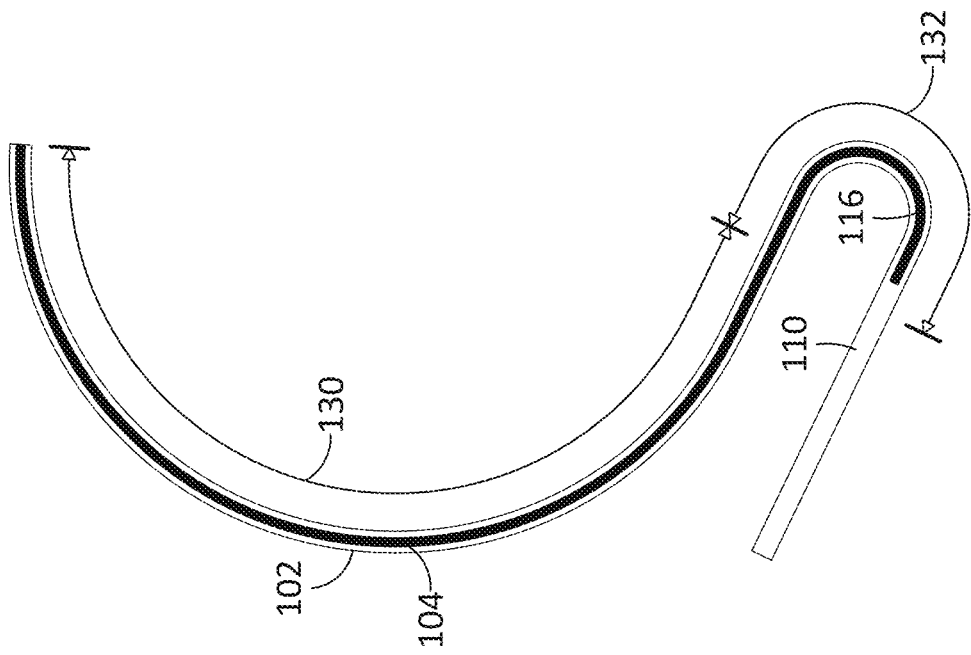
Figure 12D:
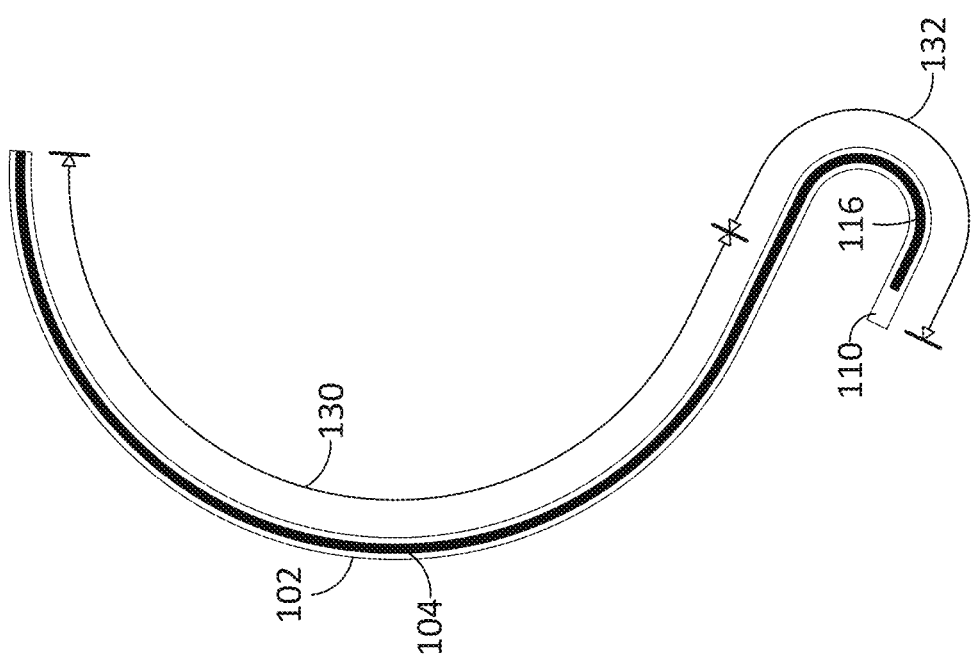

As illustrated in FIGS. 12B-12D, the distal end 116 of the inner articulating member 104, and thus the distal end 110 of the outer catheter tube 102, of the intravascular device 100 may then be gradually transformed from the straight configuration into a curved configuration. In this specific embodiment, the curve configuration has a Simmons-like shape consisting of a proximal curve 130 and a distal curve 132 (see FIG. 12D). During transformation from the straight configuration to the curved configuration, in the case where the intravascular device 100 comprises the control assembly 106a (see FIGS. 8-9), the pinion collar 188 is rotated about the longitudinal axis 118 from the neutral position to a curve actuation position relative to the housing 180 of the axial translation/articulation actuator 158. In the case where the intravascular device 100 comprises the control assembly 106b (see FIGS. 10-11), the slide mechanism 220 is moved from its distal-most position to its proximal-most position relative to the handle body 214 of the axial translation/articulation actuator 204.

Figure 12F:
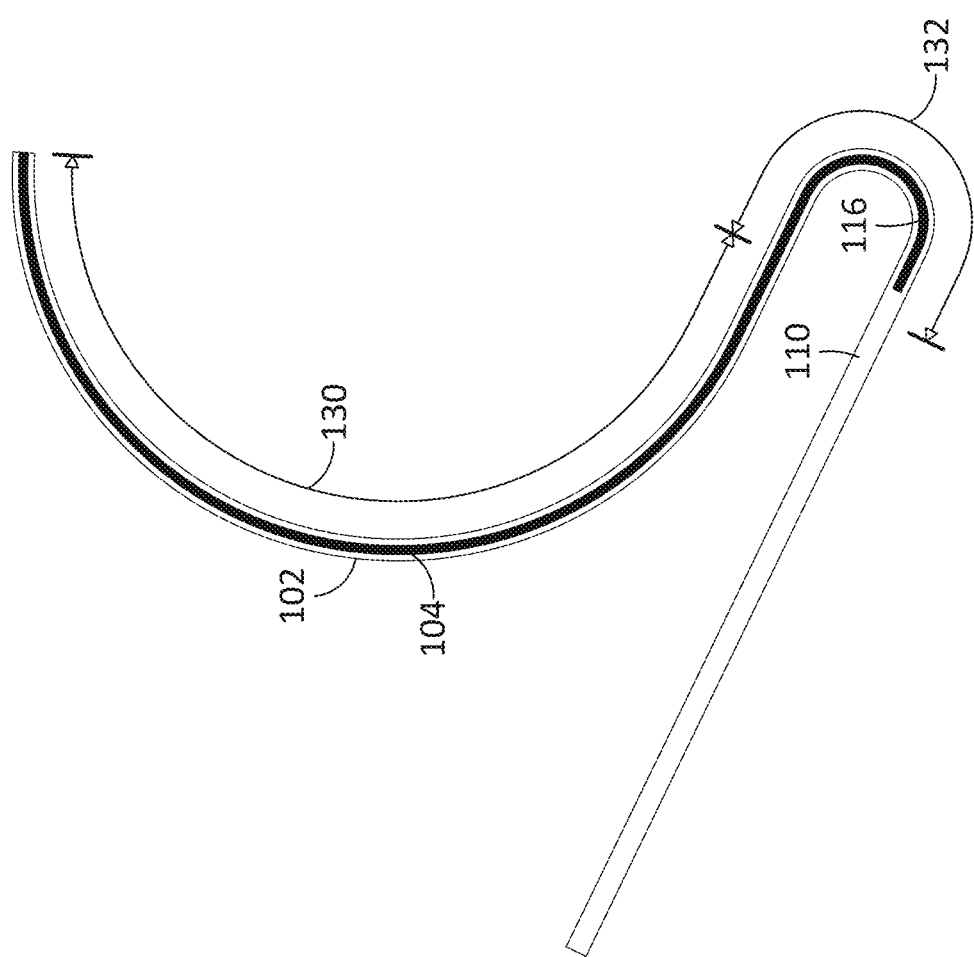

As illustrated in FIGS. 12E-12F, the distal end 100 of the outer catheter tube 102 is gradually moved from its proximal-most position to its distal-most position relative to the inner articulating member 104. In the case where the intravascular device 100 comprises the control assembly 106a (see FIGS. 8-9), this is accomplished by translating the frame 154 distally and in doing so moving the housing 180 of the axial translation/actuation actuator 158 from its distal-most position to its proximal-most position relative to the frame 154. In the case where the intravascular device 100 comprises the control assembly 106b (see FIGS. 10-11), this is accomplished by translating the frame 202 distally and in doing so moving the handle body 214 of the axial translation/actuation actuator 204 from its distal-most position to its proximal-most position relative to the frame 202.

Referring now to FIGS. 13 and 14A-14H, one exemplary method 300 of performing a medical procedure on a patient using the intravascular device 100 will be described. In the method 300, the medical procedure is a therapeutic procedure (e.g., the deployment of a stent) performed on one of the blood vessels 404 (namely one of the first arterial branch 404a that forms a left subclavian artery (LSA) 406 and a left vertebral artery (LVA) 408 extending from the aortic arch 402 of the patient, a second arterial branch 404b that forms a left common carotid artery (LCCA) 410 extending from the aortic arch 402 of the patient, and brachiocephalic trunk 404c that forms a right subclavian artery (RSA) 412, right vertebral artery (RVA) 414, and right common carotid artery (RCCA) 416 extending from the aortic arch 402 of the patient). Although the use of the intravascular device 100 lends itself well to the access of the second and third branches 404b, 404c extending from a Type III aortic arch, as illustrated in FIGS. 14A-14I, the intravascular device 100 may be used to access the first branch 404a extending from a Type III aortic arch, or any of the branches extending from a Type I aortic arch or a Type II aortic arch.

Figure 14B:
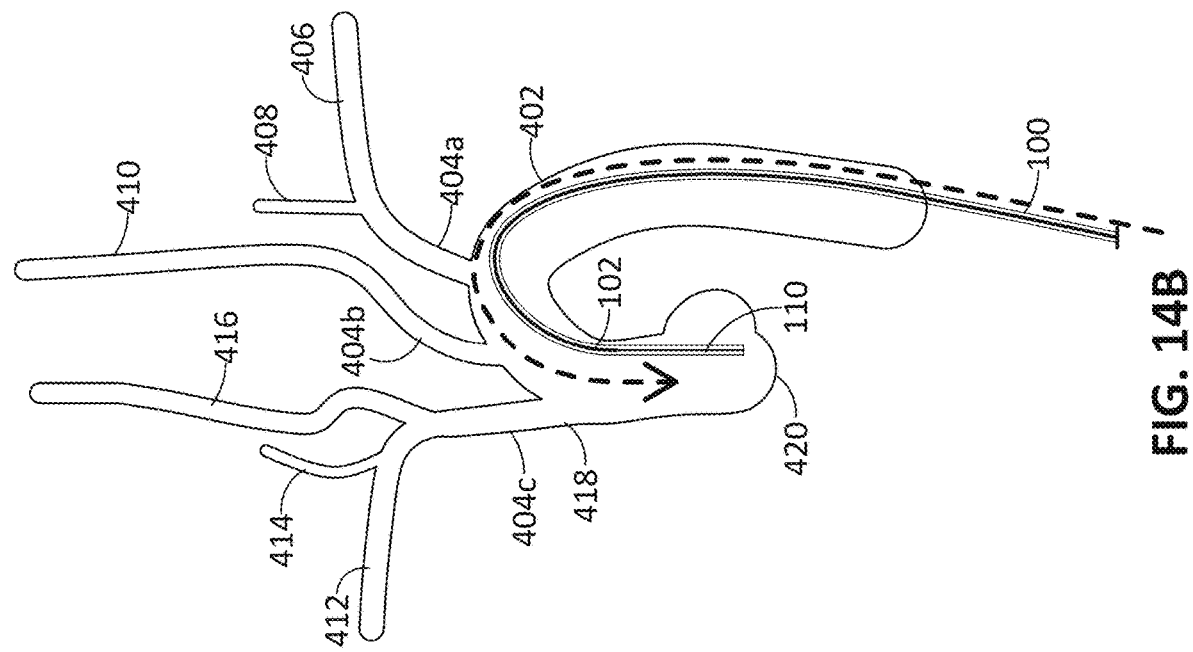
Figure 14A:
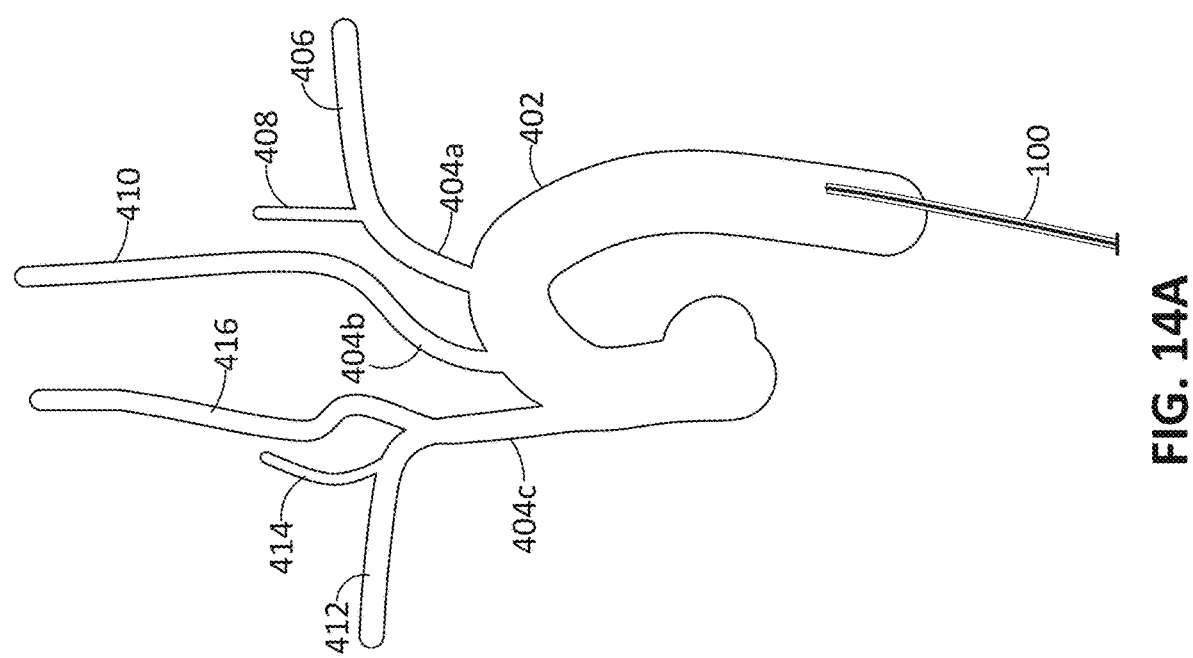
Figure 14D:
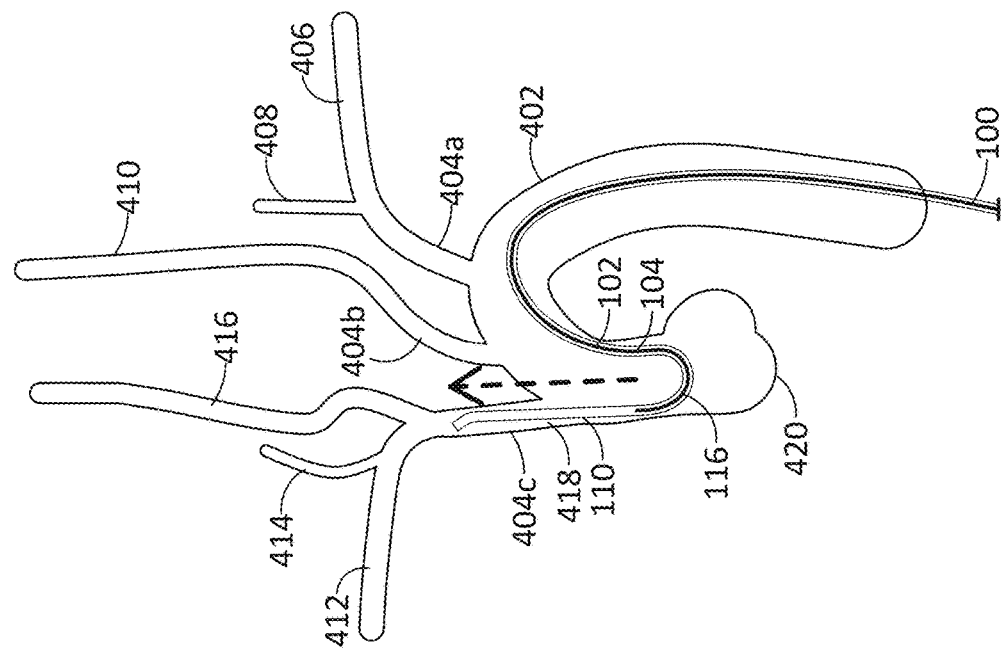
Figure 14C:
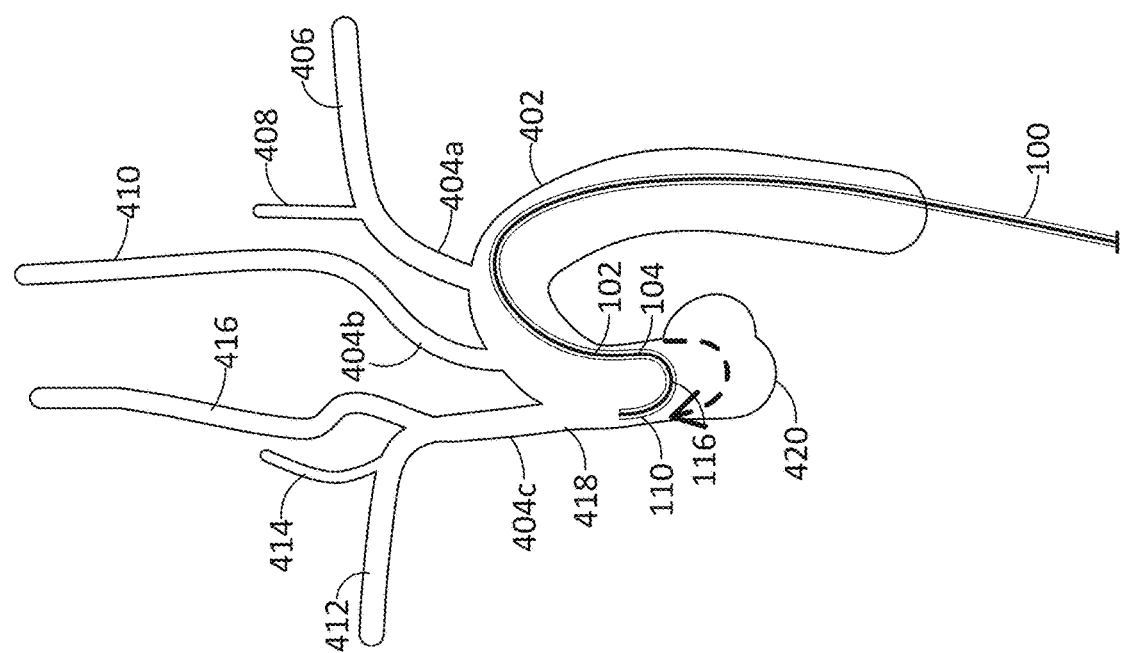

The method 300 initially comprises introducing the intravascular device 100 within the vasculature of the patient, and in this case, via a femoral approach (step 302) (see FIG. 14A). The method 300 further comprises distally advancing the intravascular device 100 within the vasculature of the patient until the distal end 114 of the outer catheter body 102 is adjacent an ostium of a blood vessel within the vasculature of the patient, and in this case, around the aortic arch 402 of the patient and adjacent the ostium 418 of the third arterial branch 404c (step 304) (see FIG. 14B). In the illustrated method, intravascular device 100 is distally advanced until the distal end 114 of the outer catheter body 102 is proximal to the aortic valve 420 of the patient.

The method 300 further comprises manipulating the intravascular device 100, such that the distal end 110 of the outer catheter body 102 points towards the ostium of the blood vessel, and in the illustrated method, the ostium of the third arterial branch 404c extending from the aortic arch 402 of the patient. In particular, the method 300 comprises actively articulating the distal end 116 of the inner articulating member 104 via manipulation of the control assembly 106 (step 306) (see FIG. 14C).

In one method, the articulated distal end 116 of the inner articulating member 104 is articulated into the proximal curve 126 that bends in a plane that emulates the curvature of the aortic arch 402 of the patient, and the distal curve 128 that bends in the same plane, but opposite the proximal curve 126, such that the distal end 116 of the inner articulating member 104, and thus the distal end 110 of the outer catheter body 102, points towards the ostium of the third arterial branch 404c extending from the aortic arch 402 of the patient. In an alternative method, the articulated distal end 116 of the inner articulating member 104 is articulated into a single curve that points the distal end 116 of the inner articulating member 104, and thus the distal end 110 of the outer catheter body 102, toward the ostium of the third arterial branch 404c extending from the aortic arch 402 of the patient, while the portion of the inner articulating member 104 residing along the length of the aortic arch 402 of the patient is passively articulated by the pressure exerted on the inner articulating member 104 by the inner wall of the aortic arch 402.

If the ostium of the third arterial branch 404c does not reside within the plane of the distal curve 128 of the articulated distal end 116 of the inner articulating member 104, the method 30 may comprise actively rotating the distal end 110 of the outer catheter body 102 about the longitudinal axis 118 while the distal end 116 of the inner articulating member 104 is articulated, until the ostium of the third arterial branch 404c does reside within the plane of the distal curve 128 of the articulated distal end 116 of the inner articulating member 104 (step 308).

The method 300 further comprises inserting the distal end 110 of the outer catheter body 102 into the ostium of the blood vessel, and in the illustrated method, the ostium of the third arterial branch 404c extending from the aortic arch 402 of the patient. In particular, the distal end 110 of the outer catheter body 102 is inserted into the ostium of the third arterial branch 404c by distally translating the distal end 110 of the outer catheter body 102 relative to the distal end 116 of the inner articulating member 104 (step 310) (see FIG. 14D).

Significantly, as the distal end 110 of the outer catheter body 102 is translated distally relative to the distal end 116 of the inner articulating member 104, the articulated distal end 116 of the inner articulating member 104 imposes a dynamic curve on the outer catheter body 102. That is, as the outer catheter body 102 is translated distally relative to the inner articulating member 104, the curve imposed on the outer catheter body 102 by the articulated distal end 116 of the inner articulating member 104 remains static relative to the aortic arch 402 of the patient, but moves relative to the outer catheter body 102 itself. Thus, in contrast to a selective catheter that has a static curve that cannot be moved relative to the body of the selective catheter, and thus may prevent or hinder the distal end of the selective catheter from being introduced into an ostium of a blood vessel, the dynamic curve imposed on the outer catheter body 102 by the articulated distal end 116 of the inner articulating member 104 does not hinder the introduction of the distal end 110 of the outer catheter body 102 into an ostium of a blood vessel, and in this case the ostium of the third arterial branch 404c.

Figure 14F:
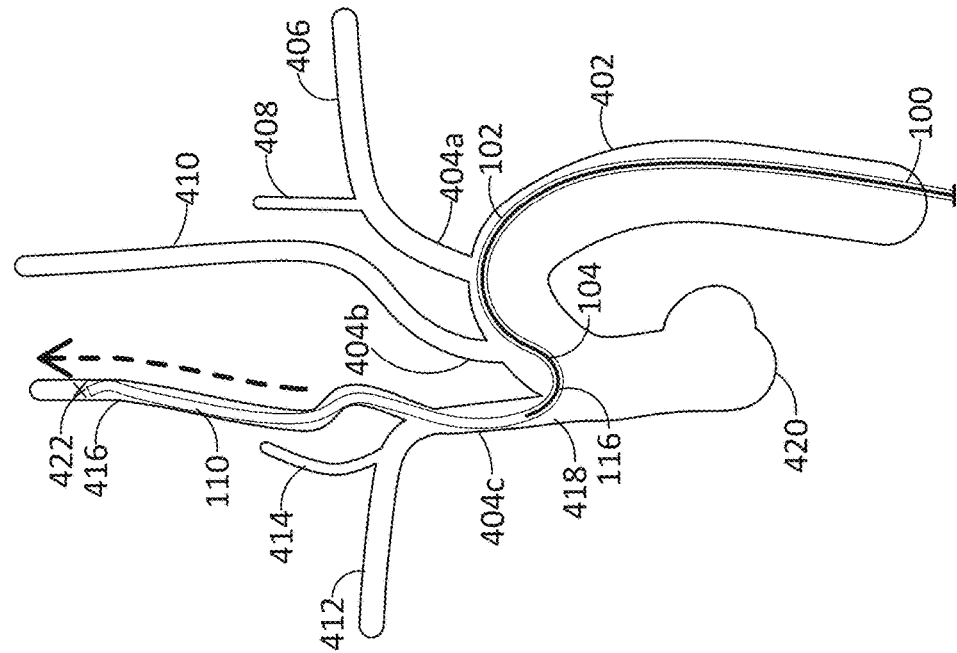
Figure 14E:
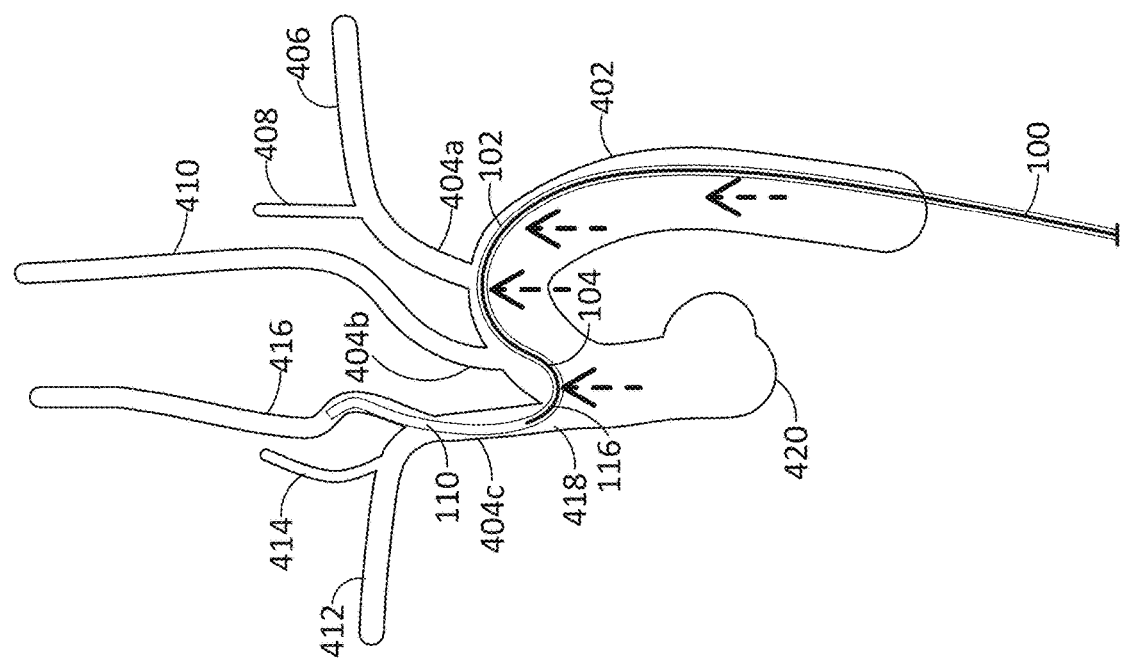

The method 300 further comprises pulling the intravascular device 100 in the proximal direction, such that the dynamic curve of the outer catheter body 102 is cinched up against the outer curvature of the aortic arch 402 of the patient (i.e., the portion of the wall of the aortic arch 402 from which the arterial branches 404 extend) (step 312) (see FIG. 14E). As a consequence, the aortic arch 402 supports, and thus, stabilizes the distal end of the intravascular device 100, and the distal end 110 of the outer catheter body 102 is distally advanced further into the third arterial branch 404c extending from the aortic arch 402 of the patient, and in this case, into the RCCA 416.

The method 300 further comprises distally translating the distal end 110 of the outer catheter body 102 relative to the distal end 116 of the inner articulating member 104, such that the distal end 110 of the outer catheter body 102 is further advanced into the blood vessel, and in this case, further advanced into the RCCA 416 at a therapeutic target site 422 (step 314) (see FIG. 14F). In this manner, the distal end of the intravascular device 100 is further anchored within the aortic arch 402 of the patient, while also providing access to the therapeutic target site 422 in the RCCA 416.

The method 300 further comprises advancing a guide catheter 424 over the intravascular device 100, while the distal end 110 of the outer catheter body 102 remains in the RCCA 416, until the distal end of the guide catheter 424 reaches the target therapeutic site 422 (step 316) (see FIG. 14G). In the illustrated method, this can be accomplished by detaching the control assembly 106a or control assembly 106b from the proximal end 108 of the outer catheter body 102, removing the inner articulating member 104 from the inner lumen 112 of the outer catheter body 102 by pulling the detached control assembly 106a or detached control assembly 106b, and threading the distal end of the guide catheter 424 over the proximal end 108 of the outer catheter body 102.

Figure 14I:
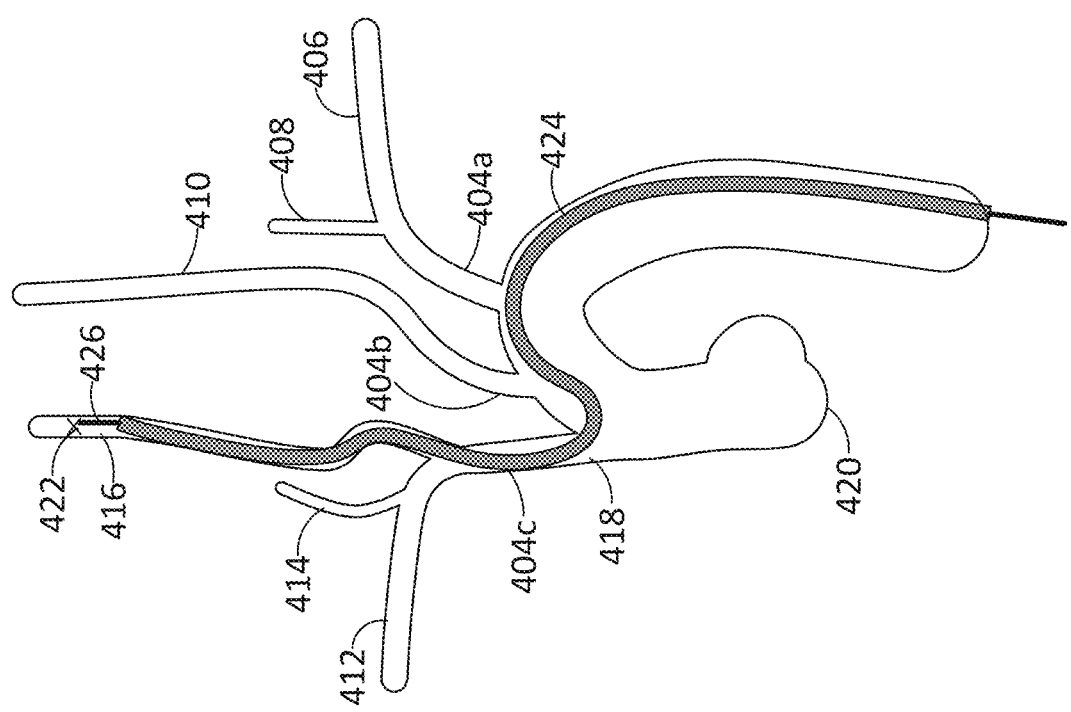

The method 300 further comprises removing the intravascular device 100 (and in particular, the outer catheter body 102 of the intravascular device 100) from the guide catheter 424 while the distal end of the guide catheter 424 remains at the target therapeutic site 422 (step 318) (see FIG. 14H), and introducing a therapeutic device 426 (and in this case, a stent delivery catheter) through the guide catheter 424 until the distal end of the therapeutic device 426 is located at the target therapeutic site 422 (step 320) (see FIG. 14I).

In the alternative embodiment where the outer catheter body 102 of the intravascular device 100 takes the form of a guide catheter, instead of advancing the guide catheter 424 over the intravascular device 100 at step 316, removing the intravascular device 100 from the guide catheter 424 at step 318, and introducing the therapeutic device 426 through the guide catheter 424 at step 320, the method 300 alternatively comprises removing the inner articulating member 104 from the inner lumen 112 of the outer catheter body 102 (step 322), and introducing the therapeutic device 426 (and in this case, a stent delivery catheter) through the inner lumen 112 of the outer catheter body 102 until the distal end of the therapeutic device 426 is located at the target therapeutic site 422.

Lastly, the method 300 comprises performing a therapeutic procedure at the target therapeutic site 422 using the therapeutic device 426, and in particular, deploying a stent in the RCCA 416 at the target therapeutic site 422 (step 326).

Referring now to FIGS. 15 and 16A-16G, another exemplary method 350 of performing a medical procedure on a patient using the intravascular device 100 will be described. In the method 350, the medical procedure is a diagnostic procedure (e.g., the introduction of an imaging (e.g., angiographic) dye) performed on one of the arterial branches 404.

Notably, in contrast to the method 300 described above with respect to FIG. 13, wherein the intravascular device 100 is used as a stable rail over which a guide catheter is introduced, and a separate therapeutic device is used to perform the medical procedure, the intravascular method 350 uses the intravascular device 100, itself, to perform the medical procedure.

Figure 16B:
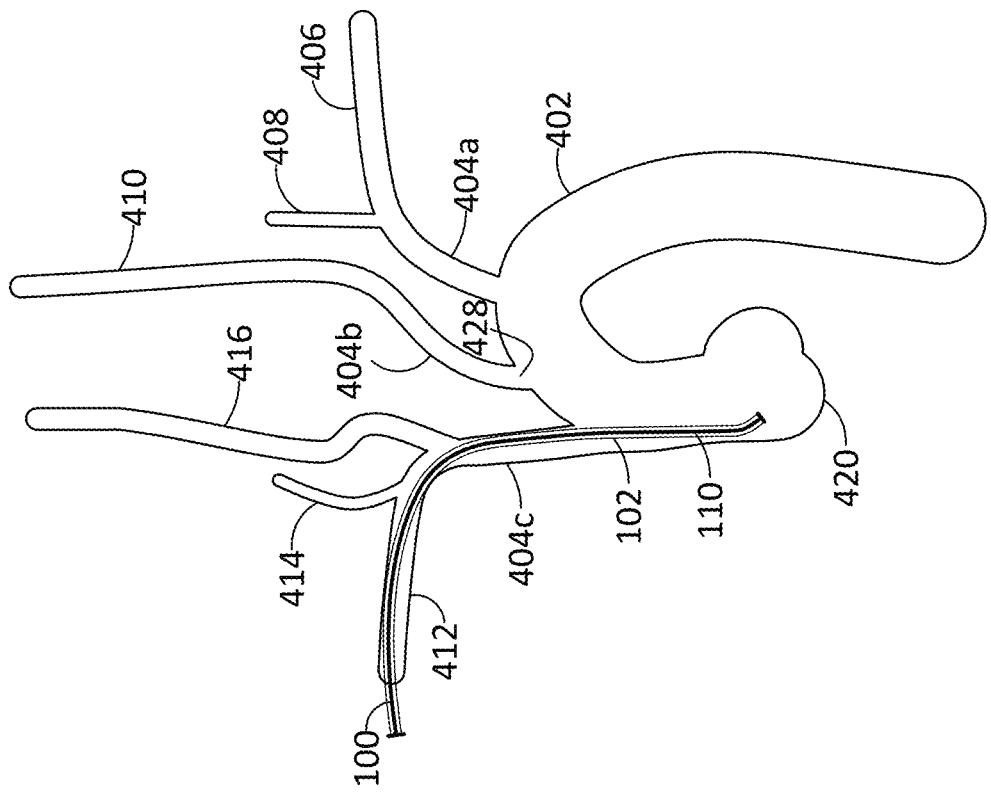
Figure 16A:
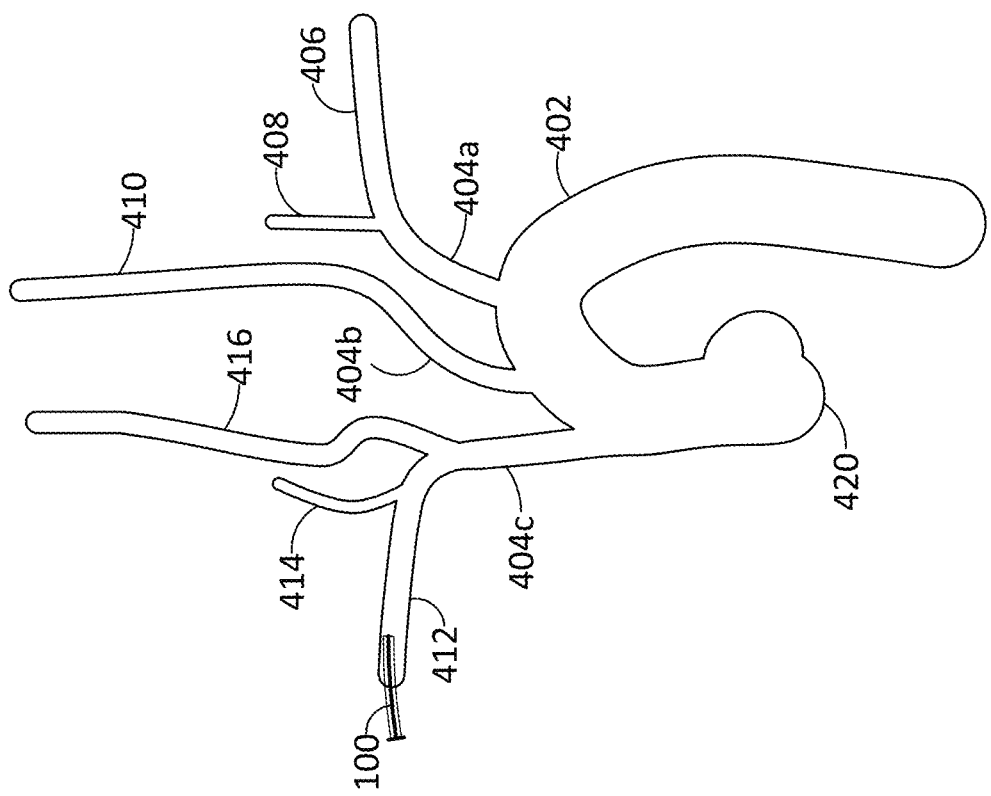

The method 350 initially comprises introducing the intravascular device 100 within the vasculature of the patient, and in this case, via a radial approach (step 352) (see FIG. 16A). The method 350 further comprises distally advancing the intravascular device 100 within the vasculature of the patient until the distal end 114 of the outer catheter body 102 is adjacent an ostium of a blood vessel within the vasculature of the patient, and in this case, through the RSA 410, through the third arterial branch 404c, and into the aortic arch 402 adjacent the ostium 428 of the second arterial branch 404b (step 354) (see FIG. 16B). In the illustrated method, intravascular device 100 is distally advanced until the distal end 114 of the outer catheter body 102 is proximal to the aortic valve 416 of the patient.

The method 350 further comprises manipulating the intravascular device 100, such that the distal end 110 of the outer catheter body 102 points towards the ostium of the blood vessel, and in the illustrated method, the ostium of the second arterial branch 404b extending from the aortic arch 402 of the patient.

Figure 16C:
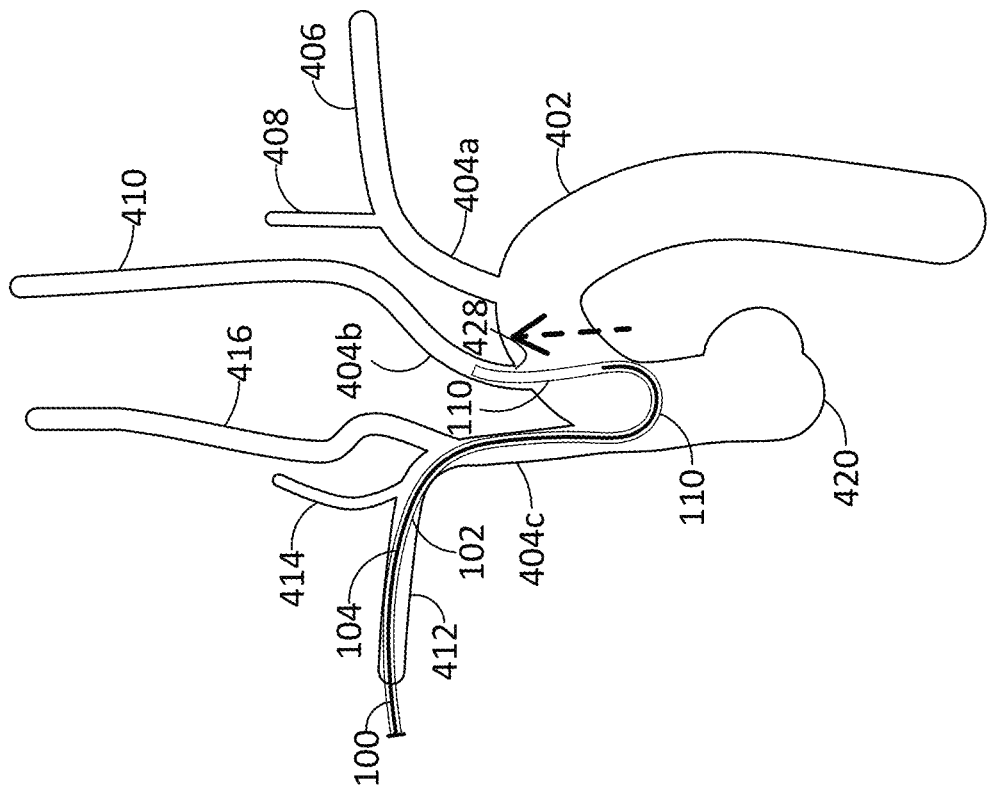
Figure 16D:
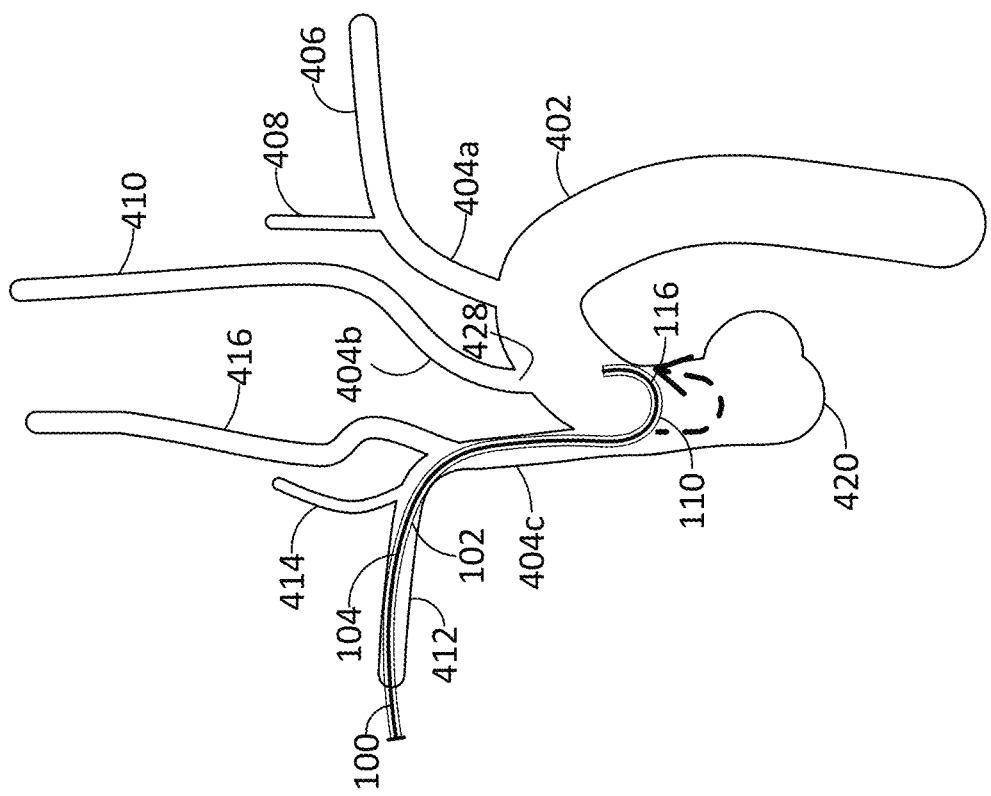

In particular, the method 350 comprises actively articulating the distal end 116 of the inner articulating member 104 (step 356) (see FIG. 16C). In the illustrated method, articulation of the distal end 116 of the inner articulating member 104 may be accomplished in the same manner described above with respect to step 306 of the method 300. In this method, the articulated distal end 116 of the inner articulating member 104 is articulated into a single curve that points the distal end 116 of the inner articulating member 104, and thus the distal end 110 of the outer catheter body 102, toward the ostium of the second arterial branch 404b extending from the aortic arch 402 of the patient, while the portion of the inner articulating member 104 residing along the length of the RSA 410 and the second arterial branch 404b is passively articulated by the pressure exerted on the inner articulating member 104 by the inner wall of the RSA 410 and second arterial branch 404b.

If the ostium of the second arterial branch 404b does not reside within the plane of the curve of the articulated distal end 116 of the inner articulating member 104, the method 350 may comprise actively rotating the distal end 110 of the outer catheter body 102 about the longitudinal axis 118 while the distal end 116 of the inner articulating member 104 is articulated, until the ostium of the second arterial branch 404b does reside within the plane of the curve of the articulated distal end 116 of the inner articulating member 104 (step 358). In the illustrated method, rotation of the outer catheter body 102 about the longitudinal axis 118 in the same manner described above with respect to step 308 of the method 300.

The method 350 further comprises inserting the distal end 110 of the outer catheter body 102 into the ostium of the blood vessel, and in the illustrated method, the ostium of the second arterial branch 404b extending from the aortic arch 402 of the patient. In particular, the distal end 110 of the outer catheter body 102 is inserted into the ostium of the second arterial branch 404b by distally translating the distal end 110 of the outer catheter body 102 relative to the distal end 116 of the inner articulating member 104 (step 360) (see FIG. 16D). Distal translation of the distal end 110 of the outer catheter body 102 relative to the distal end 116 of the inner articulating member 104 may be accomplished in the same manner described above with respect to step 310 of the method 300, with the same result of imposing a dynamic curve on the outer catheter body 102 by the articulated distal end 116 of the inner articulating member 104 that does not hinder the introduction of the distal end 110 of the outer catheter body 102 into an ostium of a blood vessel, and in this case the ostium of the second arterial branch 404b.

Figure 16F:
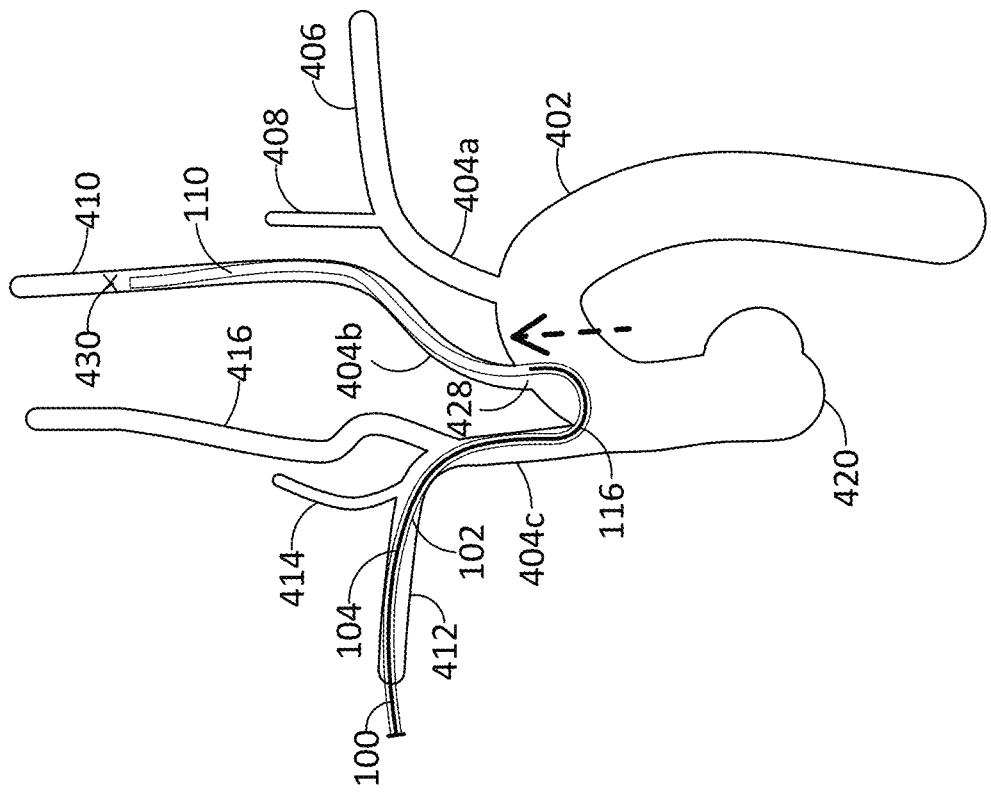
Figure 16E:
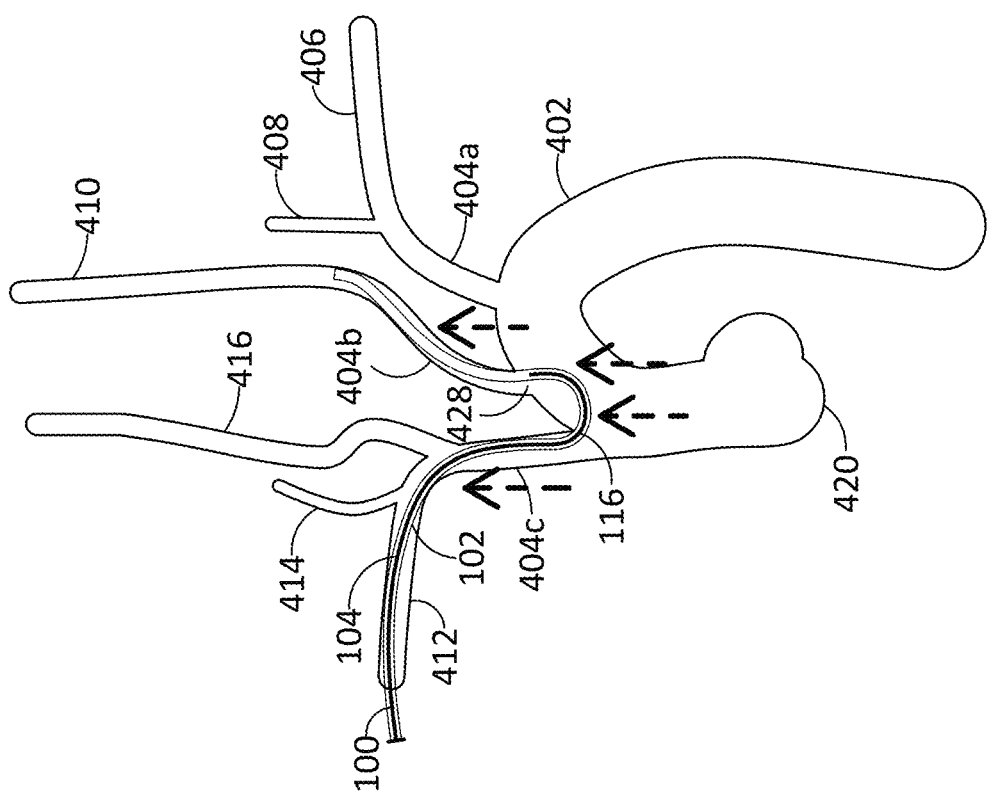
Figure 16G:
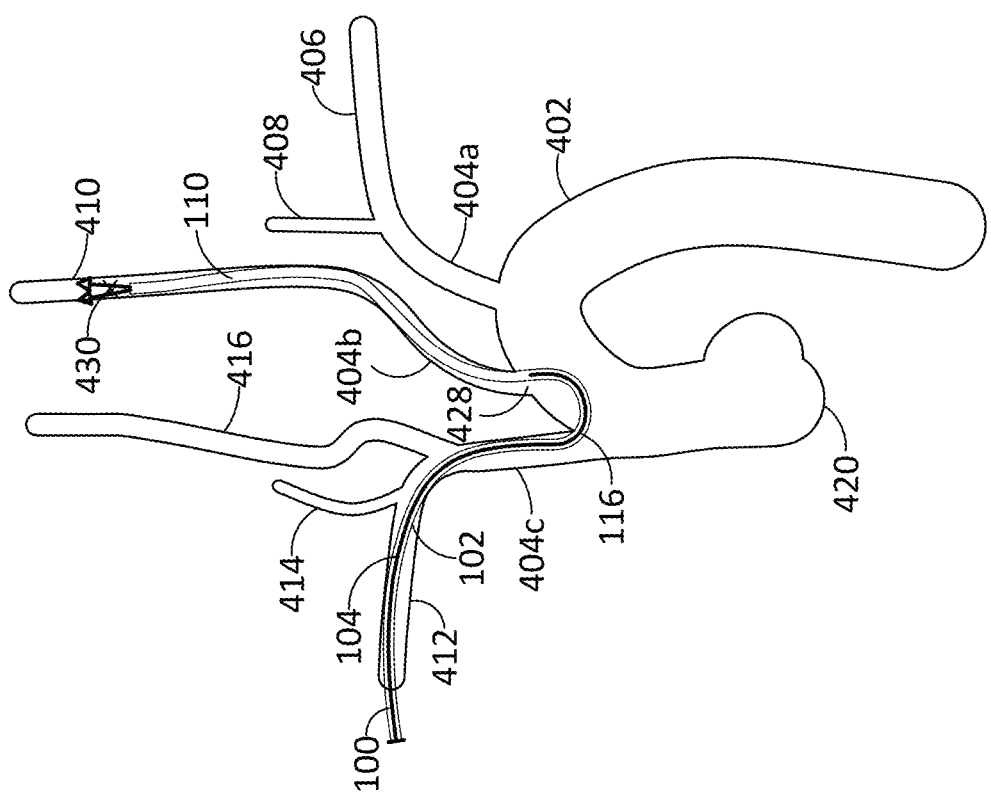

The method 350 further comprises pulling the intravascular device 100 in the proximal direction, such that the dynamic curve of the outer catheter body 102 is cinched up against the outer curvature of the aortic arch 402 of the patient (i.e., the portion of the wall of the aortic arch 402 from which the arterial branches 404 extend) (step 362) (see FIG. 16E). As a consequence, the aortic arch 402 supports, and thus, stabilizes the distal end of the intravascular device 100, and the distal end 110 of the outer catheter body 102 is distally advanced further into the second arterial branch 404c extending from the aortic arch 402 of the patient, and in this case, into the LCCA 408.

The method 350 further comprises distally translating the distal end 110 of the outer catheter body 102 relative to the distal end 116 of the inner articulating member 104, such that the distal end 110 of the outer catheter body 102 is further advanced into the blood vessel, and in this case, further advanced into the LCCA 408 at a diagnostic target site 430 (step 364) (see FIG. 16F). In this manner, the distal end of the intravascular device 100 is further anchored within the aortic arch 402 of the patient, while also providing access to the diagnostic target site 430 in the LCCA 408. Lastly, the method 350 comprises introducing an imaging dye within the LCCA 408 via the intravascular device 100 (step 366) (see FIG. 16G).

Although particular embodiments have been shown and described herein, it will be understood by those skilled in the art that they are not intended to limit the disclosed inventions, and it will be obvious to those skilled in the art that various changes, permutations, and modifications may be made (e.g., the dimensions of various parts, combinations of parts) without departing from the scope of the disclosed inventions, which is to be defined only by the following claims and their equivalents. The specification and drawings are, accordingly, to be regarded in an illustrative rather than restrictive sense. The various embodiments shown and described herein are intended to cover alternatives, modifications, and equivalents of the disclosed inventions, which may be included within the scope of the appended claims.

What is claimed is:

1. A method of performing a medical procedure on a patient using an intravascular device including an elongated outer catheter body having a distal catheter end and an inner catheter lumen, and an elongated inner member slidably disposed within the inner catheter lumen, the inner member having a distal member end, the method comprising:
   introducing the intravascular device within a vasculature of the patient;
   distally advancing the intravascular device within the vasculature of the patient until the distal catheter end is adjacent an ostium of a blood vessel within the vasculature;
   actively articulating the distal member end, such that the distal catheter end is pointed at the ostium of the blood vessel;
   inserting the distal catheter end into the ostium of the blood vessel by distally sliding the distal catheter end relative to the distal member end while the distal member end remains outside of the ostium; and distally sliding the distal catheter end relative to the distal member end, such that the distal catheter end is further advanced into the blood vessel.

2. The method of claim 1, wherein the blood vessel is an arterial branch extending from an aortic arch of the patient, and the distal member end is actively articulated, such that the distal catheter end is pointed to the ostium of the arterial branch from the aortic arch.

3. The method of claim 2, wherein the arterial branch is one of a first arterial branch that forms a left subclavian artery (LSA) and a left vertebral artery (LVA) of the patient, a second arterial branch that forms a left common carotid artery (LCCA) of the patient, and a third arterial branch that forms a right subclavian artery (RSA), right vertebral artery (RVA), and right common carotid artery (RCCA) of the patient.

4. The method of claim 2, wherein the aortic arch is a Type III aortic arch.

5. The method of claim 2, wherein the intravascular device is introduced within the vasculature of the patient via a femoral approach.

6. The method of claim 2, wherein the intravascular device is introduced within the vasculature of the patient via a radial approach.

7. The method of claim 3, wherein the arterial branch is the third arterial branch, and wherein further advancing the distal catheter end into the blood vessel comprises advancing the distal catheter end into the RCCA.

8. The method of claim 1, further comprising:
advancing a guide catheter over the intravascular device, while the distal catheter end remains in the blood vessel, until the guide catheter reaches a target therapeutic site; and
removing the intravascular device from the guide catheter while the guide catheter is at the target therapeutic site.

9. The method of claim 8, further comprising:
introducing a therapeutic device through the guide catheter until the therapeutic device is at the target therapeutic site; and
performing a therapeutic procedure at the target therapeutic site using the therapeutic device.

10. The method of claim 1, further comprising:
removing the inner member from the inner lumen of the outer catheter body;
advancing a guide catheter through the inner lumen of the outer catheter body, while the distal catheter end remains in the blood vessel, until the guide catheter reaches a target therapeutic site; and
removing the intravascular device from the guide catheter while the guide catheter is at the target therapeutic site.

11. The method of claim 10, further comprising:
introducing a therapeutic device through the inner lumen of the outer catheter body until the therapeutic device is at the target therapeutic site; and
performing a therapeutic procedure at the target therapeutic site using the therapeutic device.

12. The method of claim 1, further comprising delivering an imaging dye within the blood vessel via the catheter assembly.

13. The method of claim 1, further comprising inserting the distal member end into the ostium of the blood vessel prior to distally sliding the distal catheter end relative to the distal member end, such that the distal catheter end is further advanced into the blood vessel.

14. The method of claim 2, wherein the articulated distal member end imposes a dynamic curve on the outer catheter body that remains static relative to the aortic arch as the distal catheter end is slid relative to the articulated distal member end.

15. The method of claim 14, wherein the aortic arch has an outer curvature on which the ostium is located, and wherein the dynamic curve of the outer catheter body is located away from the outer curvature of the aortic arch when the distal member end is actively articulated, such that the distal catheter end is pointed at the ostium of the arterial branch, the method further comprising, subsequent to inserting the distal catheter end into the ostium of the arterial branch, but prior to further advancing the distal catheter end into the arterial branch, pulling the intravascular device in a proximal direction, such that the dynamic curve of the outer catheter body is cinched up against the outer curvature of the aortic arch.

16. The method of claim 1, wherein the distal catheter end, while located distal to the articulated distal member end, is distally slid relative to the distal member end, such that the distal catheter end is further advanced into the blood vessel.

17. The method of claim 1, wherein the intravascular device includes a control assembly to which a proximal catheter end of the outer catheter body and the proximal member end of the inner member is mechanically coupled, wherein the distal catheter end is distally slid relative to the articulated distal member end by manipulating an actuator of the control assembly.

18. The method of claim 17, wherein the distal member end is actively articulated by manipulating the actuator of the control assembly.

19. The method of claim 17, further comprising:
detaching the control assembly from the proximal catheter end of the outer catheter body;
advancing a guide catheter over the outer catheter body after the control assembly has been detached from the proximal catheter, and while the distal catheter end remains in the blood vessel, until the guide catheter reaches a target therapeutic site; and
removing the intravascular device from the guide catheter while the guide catheter is at the target therapeutic site.

20. The method of claim 18, further comprising removing the inner member from the inner catheter lumen by pulling the detached control assembly.

* * * * *